US007935517B2

(12) United States Patent
Cai et al.

(10) Patent No.: US 7,935,517 B2
(45) Date of Patent: May 3, 2011

(54) NANOSPEARING FOR MOLECULAR TRANSPORTATION INTO CELLS

(75) Inventors: Dong Cai, Cambridge, MA (US); David L. Carnahan, Needham, MA (US)

(73) Assignee: NanoLab, Inc., Waltham, MA (US)

( * ) Notice: Subject to any disclaimer, the term of this patent is extended or adjusted under 35 U.S.C. 154(b) by 627 days.

(21) Appl. No.: 11/233,481

(22) Filed: Sep. 22, 2005

(65) Prior Publication Data

US 2007/0231908 A1 Oct. 4, 2007

Related U.S. Application Data

(60) Provisional application No. 60/612,453, filed on Sep. 22, 2004, provisional application No. 60/697,137, filed on Jul. 7, 2005, provisional application No. 60/697,232, filed on Jul. 7, 2005.

(51) Int. Cl.
 *C12M 1/42* (2006.01)
(52) U.S. Cl. ........................ 435/285.3; 977/746; 977/748
(58) Field of Classification Search ........................ None
See application file for complete search history.

(56) References Cited

U.S. PATENT DOCUMENTS

| | | | |
|---|---|---|---|
| 5,346,683 A * | 9/1994 | Green et al. | ............... 423/447.2 |
| 6,677,313 B1 | 1/2004 | Mathiowitz et al. | |
| 6,902,895 B2 | 6/2005 | Mirkin et al. | |
| 7,029,697 B2 | 4/2006 | Segura et al. | |
| 7,225,082 B1 * | 5/2007 | Natan et al. | ...................... 702/27 |
| 2002/0086842 A1 | 7/2002 | Plank et al. | |
| 2003/0092069 A1 | 5/2003 | Kuroda et al. | |
| 2003/0147966 A1 | 8/2003 | Franzen et al. | |
| 2003/0158474 A1 | 8/2003 | Scherer et al. | |
| 2003/0166594 A1 | 9/2003 | Blum et al. | |
| 2003/0171257 A1 | 9/2003 | Stirbl et al. | |
| 2003/0180491 A1 | 9/2003 | Hirsch et al. | |
| 2003/0212022 A1 | 11/2003 | Vogel et al. | |
| 2004/0038255 A1 | 2/2004 | Mirkin et al. | |
| 2004/0063100 A1 | 4/2004 | Wang | |
| 2004/0076681 A1 | 4/2004 | Dennis et al. | |
| 2004/0166152 A1 | 8/2004 | Hirsch et al. | |
| 2004/0176282 A1 | 9/2004 | Dalby et al. | |
| 2004/0197909 A1 | 10/2004 | McKnight et al. | |
| 2005/0090732 A1 | 4/2005 | Ivkov et al. | |
| 2005/0101020 A1 | 5/2005 | Salem et al. | |
| 2005/0136102 A1 | 6/2005 | Hoffman et al. | |

FOREIGN PATENT DOCUMENTS

WO    WO 2004/060791    7/2004

OTHER PUBLICATIONS

Davide Pantarotto et al., Translocation of bioactive peptides across cell membranes by carbon nanotubes, Chemical Communications, 2004, pp. 16-17.
Keith A. Williams et al., Carbon nanotubes with DNA recognition, Nature, Dec. 2002, p. 761, vol. 420.
Alexander Star et al., Starched Carbon Nanotubes, Angewandte Chemie International Edition, 2002, pp. 2508-2512, vol. 41, issue 14.
Jose Rojas-Chapana et al., Multi-walled carbon nanotubes for plasmid delivery into *Escherichia coli* cells, Lab on a Chip, 2005, pp. 536-539, vol. 5.
Alberto Bianco et al., Can Carbon Nannotubes Be Considered Useful Tools for Biological Applications?, Advanced Materials, Oct. 16, 2003, pp. 1765-1768, vol. 15, issue 20.
Nadine Wong Shi Kam et al., Carbon nanotubes as multifunctional biological transporters and near-infrared agents for selective cancer cell destruction, PNAS, Aug. 16, 2005, pp. 11600-11605, vol. 102, issue 33.
Timothy E. McKnight et al., Tracking Gene Expression after DNA Delivery Using Spatially Indexed Nanofiber Arrays, Nano Letters, 2004, pp. 1213-1219, vol. 4, issue 7.
Ikuo Obataya et al., Nanoscale Operation of a Living Cell Using an Atomic Force Microscope with a Nanoneedle, Nano Letters, 2005, pp. 27-30, vol. 5, issue 1.
Aliasger K. Salem et al., Multifunctional nanorods for gene delivery, Nature Materials, Oct. 2003, pp. 668-671, vol. 2.
Nadine Wong Shi Kam et al., Nanotube Molecular Transporters: Internalization of Carbon Nanotube-Protein Conjugates into Mammalian Cells, Journal of the American Chemical Society, 2004, pp. 6850-6851, vol. 126.
Robert J. Chen et al., Nanocovalent Sidewall Functionalization of Single-Walled Carbon Nanotubes for Protein Immobilization, Journal of the American Chemical Society, 2001, pp. 3838-3839, vol. 123.
Cai et al., Highly efficient molecular delivery into mammalian cells using carbon nanotube spearing, Nature Methods, Jun. 2005, 449-454, vol. 2, No. 6, Nature Publishing Group.
Harutyunyan et al., Carbon Nanotubes for Medical Applications, European Cells and Materials, 2002, 84-87, vol. 3, Suppl. 2.
Jain et al., Iron Oxide Nanoparticles for Sustained Delivery of Anti-cancer Agents, Molecular Pharmaceutics, Jan. 18, 2005, 194-205 vol. 2, No. 3.
Lubbe et al., Clinical Applications of Magnetic Drug Targeting, Journal of Surgical Research, 2001, 200-206, vol. 95, Academic Press.
Penman, Carbon nanotubes show drug delivery promise, www.NewScientist.com, Dec. 16, 2003.
Plank et al., Magnetofection: Enhancing and Targeting Gene Delivery with Superparamagnetic Nanoparticles and Magnetic Fields, Journal of Liposome Research, 2003, 29-32, vol. 13, No. 1, Marcel Dekker, Inc., New York, NY.

(Continued)

*Primary Examiner* — James S Ketter
(74) *Attorney, Agent, or Firm* — Pandiscio & Pandiscio

(57) ABSTRACT

A nanostructured molecular delivery vehicle comprising magnetic materials and configured to receive passenger biomolecules. The application of a an appropriate magnetic field having a gradient orients and drives the vehicle into a biological target, which may comprise cells, cell masses, tissue slices, tissues, etc. Under the control of the magnetic field, these vehicles can penetrate cell membranes. Then, the biomolecules carried by the vehicle can be released into the cells to perform their functions. Using this "nanospearing" technique, unprecendented high transfection efficiency has been achieved in several difficult-to-transfect cells. These include, but are not limited to, Bal 17 cells, ex vivo B cells, primary cultured cortical neurons, etc. This method advances the state of the art, providing an improved technique for the introduction of exogenous molecules to cells, with the clinical applications including, but not being limited to, drug delivery, gene therapy, vaccination, etc.

16 Claims, 20 Drawing Sheets

OTHER PUBLICATIONS

Plank et al., Localized nucleic acid delivery to living cells using nanobiotechnology approaches, 4th IEEE Conference on Nanotechnology, 2004, 242-244.

Scherer et al. Magnetofection: enhancing and targeting gene delivery by magnetic force in vitro and in vivo, Gene Therapy, 2002, 102-109, vol. 9, Nature Publishing Group.

Schillinger et al., Advances in magnetofection-magnetically guided nucleic acid delivery, Journal of Magnetism and Magnetic Materials, Mar. 7, 2005, 501-508, vol. 293.

Son et al., Magnetic Nanotubes for Magnetic-Field-Assisted Bioseparation, Biointeraction, and Drug Delivery, Journal of American Chemical Society, Mar. 15, 2005, 7316-7317, vol. 127.

Zhao et al., Nanotube implantation into mammalian cells by cationic transfection, Chem. Commun., 2004, 784-785, The Royal Society of Chemistry.

* cited by examiner

Figure 1. Carbon nanotube and Ni particle morphology. All samples were tilted 45° for SEM imaging.

P-nanotubes collected by a permanent magnet

Table 1 Summary of the nanotube spearing experiments.

| Treatment | Cell type | Nanotubes | | pEGFP-c1 | pcDNA3.1 vector | Result[a] |
|---|---|---|---|---|---|---|
| | | With nickel | Without nickel | | | |
| Spearing (3,7) | Bal17 | Yes | No | Yes | No | Fluo |
| Spearing (3,7) | Bal17 | Yes | No | No | Yes | None |
| Spearing (3,7) | Bal17 | No | No | Yes | No | None |
| Spearing (3,7) | Bal17 | No | Yes | Yes | No | None |
| Spearing (15,0) | Bal17 | Yes | No | Yes | No | Weak fluo |
| Spearing (0,15) | Bal17 | Yes | No | Yes | No | Weak fluo |
| Incubation | Bal17 | Yes | No | Yes | No | Nearly background |
| Spearing (10,10), (20,20) | Primary B cells | Yes | No | Yes | No | Fluo(20,20) |
| Spearing (10,10), (20,20) | Primary B cells | Yes | No | No | Yes | None |
| Spearing (10,10), (15,15), (20,20) | Primary neurons | Yes | No | Yes | No | Fluo(20,20) |

Fluo, fluorescent signal; none, no signal.

NANOSPEARING FOR MOLECULAR TRANSPORTATION INTO CELLS

REFERENCE TO PENDING PRIOR PATENT APPLICATIONS

This patent application:

(i) claims benefit of prior U.S. Provisional Patent Application Ser. No. 60/612,453, filed Sep. 22, 2004 by Dong Cai for SPEARING MAMMALIAN CELLS WITH CARBON NANOTUBES;

(ii) claims benefit of prior U.S. Provisional Patent Application Ser. No. 60/697,137, filed Jul. 7, 2005 by Dong Cai for A NANOSPEARING APPARATUS FOR HIGHLY EFFICIENT MOLECULE DELIVERY; and (iii) claims benefit of prior U.S. Provisional Patent Application Ser. No. 60/697,232, filed Jul. 7, 2005 by Dong Cai for A NANOSPEARING APPARATUS FOR HIGHLY EFFICIENT MOLECULE DELIVERY.

FIELD OF THE INVENTION

The present invention relates to nanomaterials in general, and more particularly to (i) a nanostructured molecular delivery vehicle for delivering molecules to a selected site, and (ii) a method for transporting molecules across a biological membrane by attaching those molecules to the nanostructured molecular delivery vehicle and then applying an appropriate magnetic field having a gradient to the nanostructured molecular delivery vehicle, whereby to cause the nanostructured molecular delivery vehicle (and the attached molecules) to pass, spear-like, through the biological membrane.

BACKGROUND OF THE INVENTION

Current techniques for biomolecule transfer are a primary bottleneck in intracellular signal manipulation in laboratory research, drug delivery and gene therapy. Typically, exogenous nucleic acids (e.g., plasmid DNA, antisense RNA, siRNA, etc.) can be used to alter intracellular gene expression upon delivery across biological membranes. Such a process, commonly referred to as transfection, can be carried out with a variety of techniques including calcium phosphate transfection, lipofection, microinjection, micropipette dialysis, microparticle bombardment, electroporation, virus infection, etc. Generally, these technologies are categorized as viral or non-viral delivery techniques.

Viral delivery techniques have generally proven to be superior to non-viral delivery techniques in terms of efficiency. However, the viral delivery techniques are intrinsically biohazardous, non-specific, and can trigger side effects in the host. Therefore, viral delivery techniques for cell transfection are generally less desirable than non-viral delivery techniques. This is particularly true for gene therapy and other in vivo applications.

Non-viral delivery techniques are generally less bio-hazardous and tend to trigger less undesirable side effects in a host. However, non-viral delivery techniques are typically less efficient than viral delivery techniques. This inefficiency in non-viral delivery techniques is typically the result of low cell viability after non-viral transfection. Such low cell viability is typically the result of cell damage resulting from mechanical impact, electric shock and/or the toxicity of the chemicals used during non-viral transfection. In other words, trauma to the cell during non-viral transfection typically results in low cell viability and, therefore, low efficiency in non-viral techniques.

Another problem associated with altering intracellular gene expression occurs when using plasmid DNAs (and/or other exogenous nucleic acids). In order to alter the expression of the target gene, the plasmids (or other exogenous nucleic acids) must ultimately enter the nucleus of the cell. However, in order to enter the nucleus, the plasmids (or other exogenous nucleic acids) have to overcome three fundamental intracellular defenses. The first defense is the cell membrane, which must be penetrated. The second defense is the lysosomes located in the cellular fluid, e.g., cytosol. Once the plasmids (or other exogenous nucleic acids) have penetrated the cell membrane, they must travel through the cellular fluid, where the lysosomes may hydrolyze the plasmids (or other exogenous nucleic acids). The third defense is the nucleus envelope, which must also be penetrated. Most transfection techniques merely generate passageways for molecules to penetrate the outer cell membrane, and are not capable of helping the molecules overcome the other intracellular defenses.

Still another problem associated with altering intracellular gene expression is the variability in the effectiveness of the transfection techniques in various cell types. More particularly, there are dramatic variances in the transfection efficiency among different cell types. Certain kinds of cells, particularly the non-dividing cells, are generally regarded as "difficult-to-transfect" cells. Significantly, these types of cells are generally those with the greatest biological significance, and hence of greatest interest with respect to altering intracellular gene expression.

To overcome the foregoing limitations of the various transfection techniques, nanomaterials have been utilized to facilitate penetration of biological membranes. Carbon nanotubes, for example, have been engulfed by the cells through the endocytotic process or by an unidentified mechanism.

Additionally, an array of carbon nanotubes, grown on a substrate, has been used as a "nail board". The target cells were positioned against the nanotube tips and then a mechanical force was applied, causing the cells to be impaled on the tubes. During this procedure, despite the trauma of impalement, the cells remained viable.

In addition, metal nanorods have been shown to penetrate cells by receptor-mediated endocytosis. One technique, sometimes referred to as magnetofection, utilizes magnetic nanoparticles to help concentrate the particle-DNA-liposome composites adjacent to the cell surface, and subsequently improves biomolecule trasfection.

Another technique, sometimes referred to as calcium phosphate transfection, takes advantage of cellular biomineralization to introduce DNA into the cells. More particularly, it has been shown that well-defined calcium phosphate-DNA nanostructures have increased transfection efficacy.

In these latest developments in nano-biotechnology, nanostructures have demonstrated promising characteristics for biomolecule delivery. A significant advantage of nanostructures is their nanoscale dimension, which facilitates high cell viability during the transfection process. In particular, the small size of the nanostructures allows them to utilize normal biological processes (e.g., endocytosis, biomineralization, etc.) to provide entry into the cells. This characteristic makes nanostructures good candidates to carry molecules across cell membranes.

It should be appreciated that, in order to carry molecules, the surfaces of the nanostructures must be adapted so that molecules can be bound onto the nanostructures by covalent bonding, electrostatic attraction, hydrophobic adsorption, etc.

Thus, to date, a number of new techniques have been developed to utilize nano-biotechnology for molecule delivery. However, all of these techniques suffer from one or more significant disadvantages, e.g., slow transfection speed, significant cell damage during transfection, difficulties binding the molecules to the nanomaterials, etc., In addition to the foregoing, because the mechanisms involved in introducing nanostructures into cells through biopassages are not completely understood, it is desirable to have a more controlled and directed way of passing nanostructures into cells. Additionally, because intracellular gene expression requires biological molecules to penetrate the nucleus of the cell, there exists a need for a more reliable method for passing the biological molecules through the cell membrane and ultimately into the nucleus.

SUMMARY OF THE INVENTION

To overcome the problems associated with traditional molecular delivery techniques, the present invention provides an improved system (method and apparatus) for delivering molecules across biological membranes. This novel approach utilizes a nanoscale molecular delivery vehicle to carry passenger molecules across the biological membranes. The nanoscale molecular delivery vehicle is configured to be relatively long and thin, and is configured so as to be oriented and driven by an appropriate magnetic field having a gradient. The nanoscale molecular delivery vehicle may be a nanotube which is either inherently magnetic or which has a magnetic core. The surface of the nanoscale delivery vehicle (e.g., the nanotube) is adapted to facilitate easy and reliable attachment of biomolecules to the nanostructure. An appropriately configured magnetic field having a gradient is used to steerably drive the molecular delivery vehicle, whereby to mechanically penetrate the membrane and deliver the passenger biomolecules to the interior of the cell. This process is sometimes referred to herein as nanospearing. Due to the nanoscale size of the delivery vehicle, neither cell function nor cell viability are significantly negatively affected by the nanospearing process. As a result, highly efficient transfection may be achieved in difficult-to-transfect cells.

The nanospearing process can be conducted in vivo, or in a laboratory, or in some other location; the target cells can be of any cell type, including non-dividing cells and including stem cells; and the delivered molecules can be for altering intracellular gene expressions, or for pharmaceutical applications, or other applications.

Thus, the present invention provides a novel system (method and apparatus) for efficiently transfecting individual cells, particularly difficult-to-transfect cells.

The present invention also provides a novel system (method and apparatus) for efficiently transfecting cells in homogenous or non-homogenous systems, including tissue samples.

The present invention also provides a novel system (method and apparatus) for efficiently delivering molecules to stem cells.

The present invention also provides a novel system (method and apparatus) for efficiently delivering molecules in vivo.

The present invention also provides a novel system (method and apparatus) for achieving high efficiency drug delivery.

In one preferred form of the invention, there is provided a molecular delivery system comprising:

a molecular delivery vehicle comprising an elongated nanostructure having a longitudinal axis, and (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and (ii) configured to receive at least one molecule of biological interest and hold the at least one molecule to the nanostructure.

In another preferred form of the invention, there is provided a suspension of magnetically driven molecular delivery vehicles contained in a fluid medium.

In another preferred form of the invention, there is provided a method for magnetically orienting and driving a nanostructured molecular delivery vehicle, comprising:

suspending the molecular delivery vehicle in a fluid medium; and applying an appropriate magnetic field having a gradient to the region about the molecular delivery vehicle so that the molecular delivery vehicle is oriented and driven spear-like through a cell membrane.

In another preferred form of the invention, there is provided a method for driving magnetic nanostructured molecular delivery vehicles towards biological targets by magnetic fields, comprising:

immersing the magnetic nanostructured molecular delivery vehicles in physiological saline;

injecting the magnetic nanostructured molecular delivery vehicles into a biological region; and applying an appropriate magnetic field having a gradient to the magnetic nanostructured molecular delivery vehicles so as to cause the magnetic molecular delivery vehicles to be oriented toward and moved toward the biological targets.

In another preferred form of the invention, there is provided a method for driving magnetic nanostructured molecular delivery vehicles towards biological targets by magnetic fields, comprising:

immersing the magnetic nanostructured molecular delivery vehicles in physiological saline;

dispersing the magnetic nanostructured molecular delivery vehicles in the vicinity of the targets; and applying an appropriate magnetic field having a gradient to the magnetic nanostructured molecular delivery vehicles so that they will be oriented toward and driven toward the biological targets.

In another preferred form of the invention, there is provided a method for driving magnetic nanostructured molecular delivery vehicles towards biological targets by magnetic fields, comprising:

immersing the magnetic nanostructured molecular delivery vehicles in physiological saline;

docking the magnetic nanostructured molecular delivery vehicles on the cell membranes by ligand molecules; and applying an appropriate magnetic field having a gradient to the magnetic nanostructured molecular delivery vehicles so that they will be oriented toward and driven toward the biological targets.

In another preferred form of the invention, there is provided a method for penetrating a biomembrane with a magnetically driven molecular delivery vehicle, comprising:

positioning the biomembrane and the magnetically driven molecular delivery vehicle in the same fluid environment;

providing an appropriate magnetic field having a gradient to orient and drive the molecular delivery vehicle toward the biomembrane; and penetrating the biomembrane with the molecular delivery vehicle.

In another preferred form of the invention, there is provided a method for delivering a molecule to a cell using a magnetic field, the method comprising:

providing a magnetically driven molecular delivery vehicle carrying the molecule;

positioning the magnetically driven molecular delivery vehicle to a liquid environment containing the cells;

providing an appropriate magnetic field having a gradient to orient and drive the magnetically driven molecular delivery vehicle toward the cell; and sustaining the magnetic field so as to cause the magnetically driven molecular delivery vehicle to penetrate the cell membrane and enter the cell.

In another preferred form of the invention, there is provided a method for sensing intracellular molecules in live cells with magnetic fields, the method comprising:

providing magnetically driven molecular delivery vehicles carrying probe molecules for probing the intracellular molecules;

positioning the magnetically driven molecular delivery vehicles in a liquid environment containing the cells;

providing an appropriate magnetic field having a gradient to orient and drive the magnetically driven molecular delivery vehicles so as to penetrate membranes of the cells;

waiting a certain period to let the probe molecules bind with the intracellular molecules;

providing an appropriate magnetic field to pull the magnetically driven molecular delivery vehicles out of the cells; and collecting the magnetically driven molecular delivery vehicles.

In another preferred form of the invention, there is provided a molecular delivery vehicle comprising a multiwall carbon nanotube with an outer shell functionalized to attach biological materials thereto, and an inner shell that encapsulates a needle-like magnetic core nanoparticle.

In another preferred form of the invention, there is provided a system for delivering molecules of biological interest to the interior of a cell, comprising:

an elongated nanostructure comprising a distal end, a proximal end, and a longitudinal axis extending between the distal end and the proximal end;

magnetic material carried by the nanostructure, the magnetic material being configured such that, when the nanostructure is positioned within an appropriate magnetic field having a gradient, the nanostructure will be oriented and driven, distal end first, in a first direction; and regions formed on the nanostructure which are configured to bind the molecules thereto.

In another preferred form of the invention, there is provided a magnetically driven molecular delivery system comprising:

a magnetic structure comprising an elongated nanostructure and magnetic material, wherein the magnetic material is configured to orient and move the magnetic structure in a direction parallel to the longitudinal axis of the elongated nanostructure when exposed to an appropriate magnetic field having a gradient;

one or more molecules of biological interest attached to the magnetic structure; and a fluid containing the magnetic structure, one or more molecules of biological interest attached to said magnetic structure, and target cells.

In another preferred form of the invention, there is provided a method for molecular delivery into a target cell comprising:

providing at least one magnetic structure by attaching magnetic material to a nanostructure;

attaching one or more molecules of biological interest to the at least one magnetic structure;

suspending the at least one magnetic structure in a fluid medium containing target cells; and applying an appropriate magnetic field having a gradient to the fluid medium so that the at least one magnetic structure (i) orients in a direction parallel to the path between the at least one magnetic structure and the target cell; and (2) moves into the target cell.

BRIEF DESCRIPTION OF THE DRAWINGS

These and other objects, features and advantages of the present invention will be more fully disclosed or rendered obvious by the following detailed description of the preferred embodiments of the invention, which is to be considered together with the accompanying drawings wherein like numbers refer to like parts and further wherein.

Figures 1A, 1B:
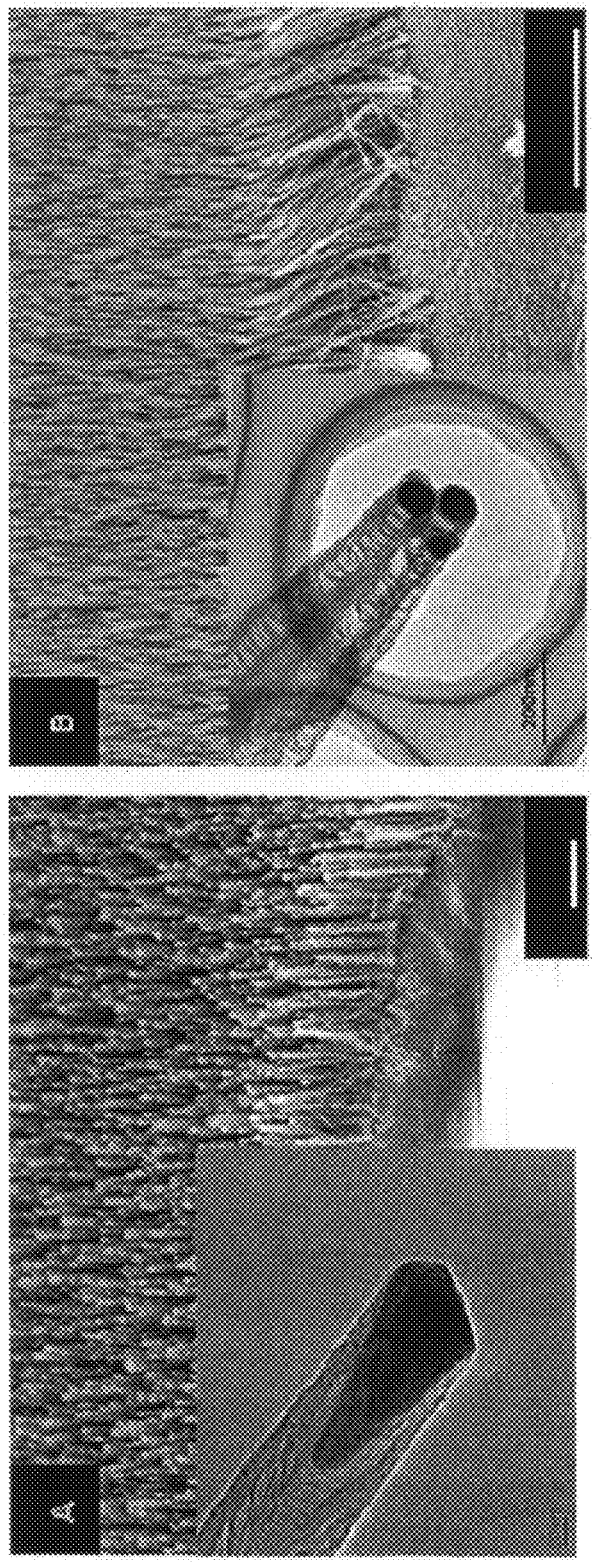
FIG. 1A is a scanning electron microscopy (SEM) image of magnetically drivable nanotubes (on a substrate) which may be used for nanospearing, with the inset (a transmission electron microscopy (TEM) image) showing elongated, nanowire-like nickel particles embedded at the tip of the nanotubes.
FIG. 1B is an SEM image of magnetically non-drivable nanotubes (on a substrate), wherein the inset is a TEM image showing nickel particles (with a prolate shape) embedded at the tips of the nanotubes.

Table 1 is a table summarizing some of the experiments conducted in support of nanospearing mediated transfection.

DETAILED DESCRIPTION OF PREFERRED EMBODIMENTS

The present invention comprises the use of magnetically driven molecular delivery vehicles to carry passenger molecules across biological membranes and, in many cases, into the nucleus, without causing substantial harm to the target cells. The molecular delivery vehicles comprise nanostructures having magnetically responsive aspects which permit the delivery vehicles to be oriented and driven by an appropriate magnetic field having a gradient, whereby to advance the delivery vehicle through a cell membrane, and the molecular delivery vehicles are configured so as to facilitate attachment of the passenger molecules to the delivery vehicles.

In one preferred embodiment of the present invention, carbon nanotubes are used as the molecular delivery vehicles to transport biomolecules across the cell membranes.

The carbon nanotubes may be grown in bulk by chemical vapor deposition (CVD) techniques or grown aligned on substrates by plasma enhanced chemical vapor deposition (PECVD) techniques. If the nanotubes are grown aligned on substrates, the nanotubes are scraped off the substrate and transferred into suspension. The nanotubes can be dispersed for tens of minutes in an organic solvent (e.g., ethyl alcohol) using ultrasonication without any surfactant.

These nanotubes have a magnetic metal nanoparticle (e.g., iron, cobalt, nickel, etc.) or other magnetic nanoparticle attached to the nanotube. As used herein, the term "magnetic nanoparticle" is meant to include any nanoparticle which moves in response to being placed in an appropriate magnetic field. This term is meant to specifically include ferromagnetic, paramagnetic and diamagnetic materials. Preferably the magnetic metal nanoparticle is incorporated in the nanotube's tip. The magnetic metal nanoparticle is incorporated in the nanotube so that the nanotube will respond to an applied magnetic field and its gradient such that the nanotube can be oriented and driven through, the suspension by the magnetic field and its gradient. The nanotubes can then perform linear, circular, impulsive, spinning, or other movements through the suspension, depending on the properties of the magnetic field which is applied to the nanotube.

In one form of the present invention, the nanotubes in the suspension are driven towards cells which are cultured on a substrate. The substrate is placed in the suspension so that the target cells are substantially stationary, and then an appropriate magnetic field is applied so that the nanotubes are driven, point first, through the membranes of the target cells, whereby to deliver their passenger molecules to the interiors of the cells. In one preferred form of the invention, the cells are intially speared by immersing them in the nanotube suspension and then adjusting the magnetic field so as to induce movement of the nanotubes towards and into the cells. Then the cells are preferably transferred to culture dishes, where a permanent magnet enhances spearing by applying a static field.

Thus, if enhanced green fluorescent protein (EGFP) plasmids (or other molecules) are immobilized on the nanotubes beforehand, the EGFP plasmids (or other molecules) will be delivered to the interiors of the cells and the EGFP plasmids (or other molecules) can be expressed (or otherwise released) in the cells.

In practice, such transfection, observed under a fluorescence microscope, has been found to be effective for almost 100% of Bal-17 cells and ex vivo B cells, and more than 80% of primary cortical neurons.

It should be appreciated that not all nanotubes are steerable and/or drivable by a magnetic field. More particularly, it has been found that the nanotubes must be carefully configured so as to render them steerable and/or drivable by a magnetic field. The response of a nanotube to a magnetic field can be demonstrated by placing a container of the nanotube suspension on a standard laboratory magnetic stir plate without a magnetic stirring bar in the container. If the nanotubes can be magnetically steered and driven, they will move, in synchronization with the magnetic field, and a moving "cloud" will be visible to the naked eye.

In addition to applying a magnetic field to the nanotubes in order to determine if the they can be magnetically driven, one can also observe the structure of the nanotubes using transmission electron microscopy (TEM).

It has been determined, and looking now at FIG. 1A, that steerable and drivable nanotubes are generally relatively short (e.g., <2 μm) and typically have diameters of less than approximately 200 nanometers, and have a magnetic particle with an aspect ratio of approximately >2:1 and, preferably, around 3:1. (See FIG. 1A, where the length of the nanotubes is approximately 1.5 μm, the scale bar is 1.5 μm, and the particle aspect ratio is 2.9±0.13.) As used herein, the term aspect ratio is intended to mean the ratio of the particle's length to the particle's width. The longitudinal axis of the nanoparticle is substantially aligned with the longitudinal axis of the nanotube.

In contrast, and as shown in FIG. 1B, non-steerable and/or non-drivable nanotubes are typically much longer (e.g., >15 μm) and have a magnetic particle with an aspect ratio of about 1 or less. (See FIG. 1B, where the length of the nanontubes is approximately 15 μm, the scale bar is 10 μm, and the particle aspect ratio is 0.7±0.04.)

As noted above, the nanotubes are preferably placed in suspension so that they can be driven towards target cells which are immobilized on a substrate or otherwise relatively stationary within the suspension. More particularly, and in accordance with one preferred embodiment of the present invention, the nanotubes may be suspended in fluid, e.g., physiological saline. In addition, as will hereinafter be discussed, it is also possible to deliver a nanotube-containing suspension to cells at another location, e.g., an anatomical site.

As noted above, the nanotubes are configured so that passenger molecules may be attached thereto, whereby the passenger molecules may be carried through a cell membrane by the nanotubes.

In one preferred embodiment of the present invention, the nanotubes are grown so as to be characterized by an uneven, "bamboo-like" structure. Looking now at the inset of FIGS. 1A and 1B, such a bamboo structure can be seen. This bamboo structure is an important feature of the nanotube. More particularly, unlike a traditional hollow nanotube, which has carbon shells lined up concentrically along the axis of the nanotube, the preferred bamboo structure has sidewalls composed of distinct carbon "cups" which are stacked, one on top of another, thereby forming a sleeve out of the stacked carbon cups. The graphene walls terminate at the rims of the cups, along the outer surface of the nanotube, where dangling bonds may be formed. Therefore, more dangling bonds may be formed at the surface of the bamboo carbon nanotube than with the traditional, hollow nanotube variety, which typically only has such dangling bonds formed at each end (i.e., if the hollow nanotube has no hemispherical cap). These dangling bonds are highly advantageous, since they create a point for robust biomolecule attachment.

These bamboo-structured nanotubes can be created using both CVD and PECVD techniques, and the high concentration of attachment sites along their surface facilitates the chemical attachment of biomolecules.

Figure 1C:
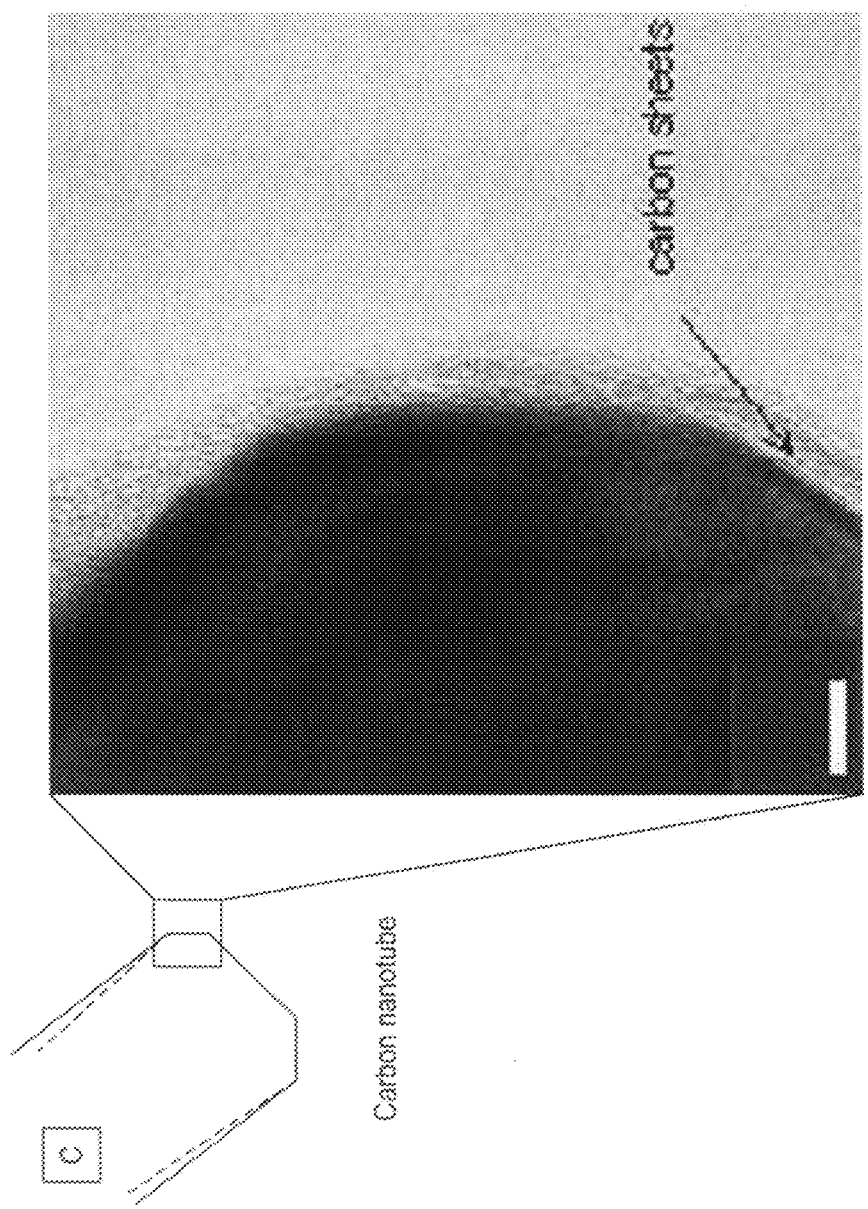
FIG. 1C is a TEM image of the magnetic particles enclosed in the nanotubes, wherein the inset is a transmission electron microscopy (TEM) image showing elongated, wire-like nickel particles embedded at the tips of the nanotubes.

For the purpose of molecular delivery, it is desirable for the magnetic particle, or particles, to be well encapsulated within the nanotube, so that the magnetic particle (or particles) do not migrate during nanotube motion. FIG. 1C shows a high-resolution TEM image where the magnetic particles are completely enclosed in the nanotube by layers of graphene sheet and amorphous carbon. If the magnetic particles are not well encapsulated in the nanotube, the magnetic particles may detach from the remainder of the nanotube, thereby raising the possibility of intracellular metal contamination. For example, $Ni^{2+}$ can alter cellular signal transduction, e.g., gene expression.

As noted above, in one preferred embodiment of the present invention, an appropriate magnetic field having a gradient orients and drives the nanotubes in a medium (e.g., water) toward cells cultured on a substrate. After preliminary spearing (effected by moving the nanotubes in the magnetic field), the cells are transferred to culture dishes above a permanent magnet so that the static field of the permanent magnet enhances cell penetration by the nanotubes.

Figures 2A, 2B:
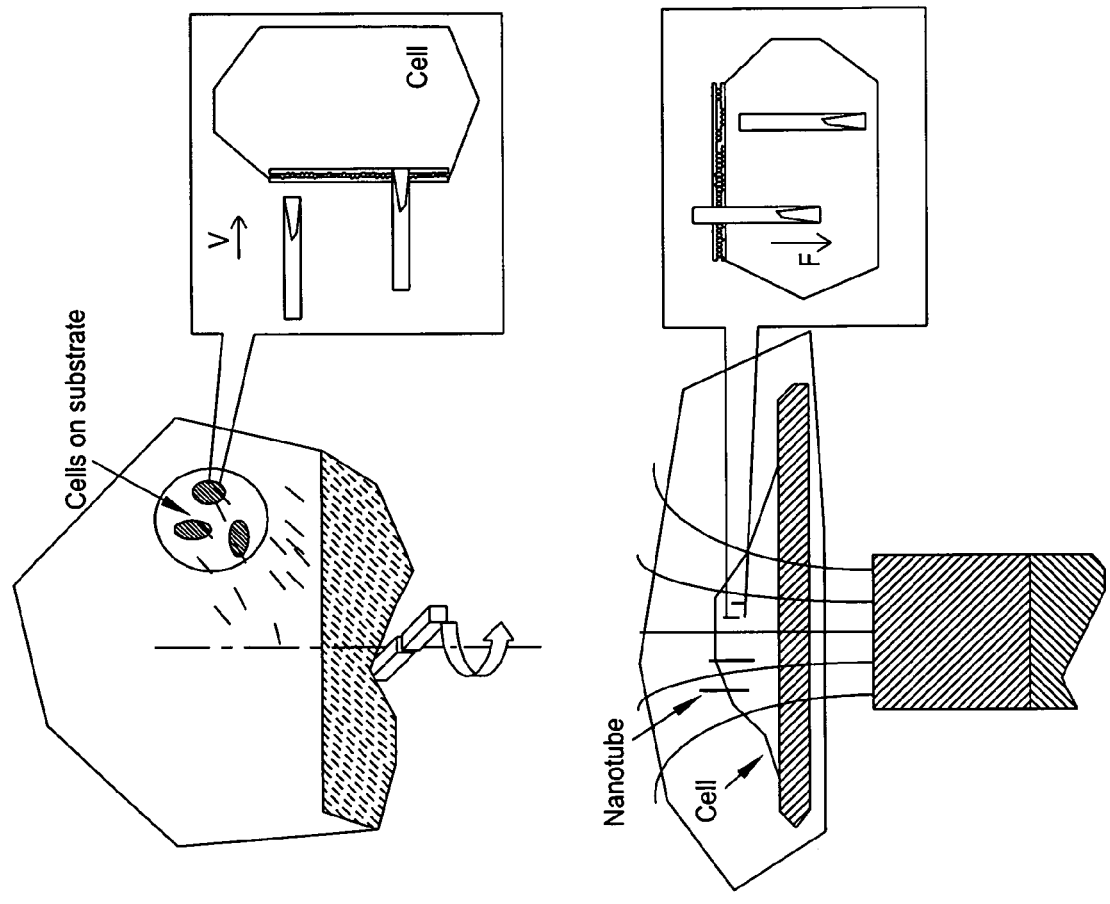
FIGS. 2A and 2B are schematic diagrams illustrating the nanospearing process of the present invention.

This two-step procedure is schematically illustrated in FIGS. 2A and 2B. In the first step (see FIG. 2A), a rotating magnetic field drives the nanotubes (illustrated as short black lines in FIG. 2A) so that they spear the target cells (shown as yellow spots in FIG. 2A) which are immobilized on a substrate. The boxed inset in FIG. 2A is a close-up of one such cell, with a nanotube penetrating the cell's membrane. The vector v represents the speed of the nanotubes. The plasma membrane of the cell is illustrated as the assembly of red circles in FIG. 2A.

In the second step, illustrated in FIG. 2B, a static field persistently pulls the nanotubes into the cells. The vector F represents the direction in which the magnetic force is applied.

The following examples illustrate some preferred forms of the present invention. It is to be understood that the present invention is not intended to be limited to the particular constructions disclosed in the following examples, rather, the examples are provided to help illustrate the breadth of the present invention.

Example 1

In one embodiment of the present invention, cells were dispersed on poly(D-lysine)-coated substrates, (e.g., grids and cover slips). A beaker, containing 10 ml of serum-free Dulbecco's Modified Eagle Medium supplemented with magnetically-drivable nanotubes (0.1 pM), was placed on a magnetic stirrer (Fisher Scientific) at room temperature. The substrates were then picked up with tweezers and vertically placed into the beaker, with the cells facing in the direction of the "incoming" nanotubes. The speed of the stirrer was set at 1,200 r.p.m. so as to cause the nanotubes to be driven spear-like into the stationary target cells. Thereafter, in order to enhance the nanospearing with a static magnetic field, the cell substrates were transferred to a cell dish, and the cell dish was laid on a Nd—Fe—B permanent magnet. An adaptor, comprising grooves machined on its surface, was sandwiched between the cell dish and the Nd—Fe—B permanent magnet so as to produce a stray field with high gradients in close proximity and thereby improve the magnetic force. Thus, in this example, the magnetic stirrer causes the magnetically-drivable nanotubes to move in a predetermined pattern within the medium, such that the nanotubes are oriented toward and driven against the stationary cells, and then the permanent magnet is used to apply a static magnetic field so as to enhance the nanospearing action.

Example 2

Figure 3B:
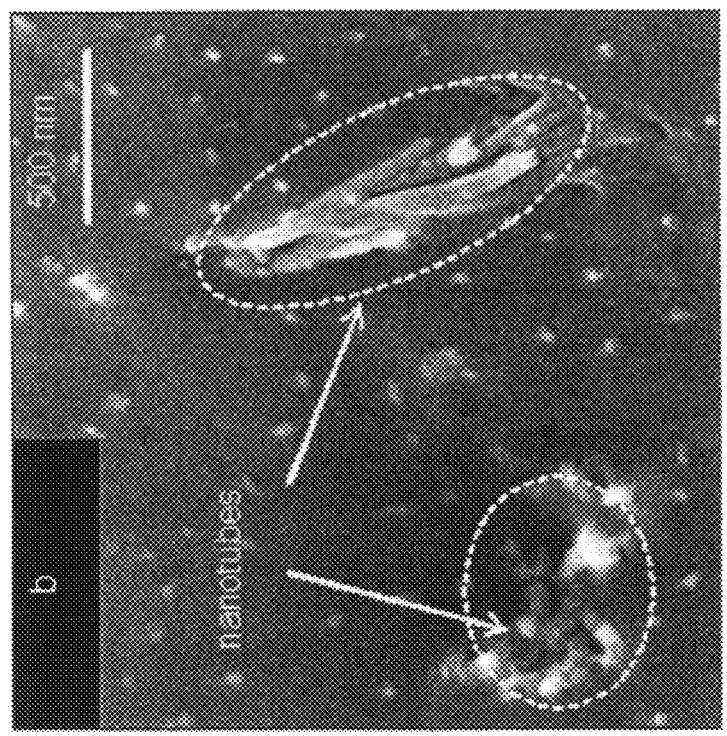
FIGS. 3A and 3B are SEM images of the membranes of MCF-7 cells.
Figure 3A:
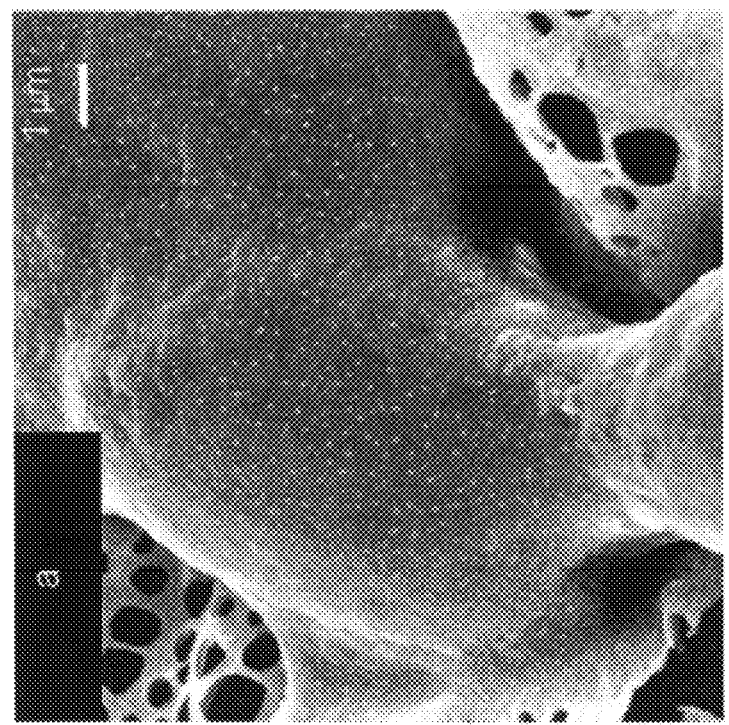

MCF-7 cells were subjected to nanospearing in accordance with the two-step nanospearing procedure discussed above. The typical membranes of MCF-7 cells that were cultured on a grid in this experiment are shown in FIGS. 3A and 3B. FIG. 3A is an image showing the cells without nanospearing, and FIG. 3B is an image showing the cells with nanospearing. Scale bars in FIGS. 3A and 3B are 1 µm and 500 nm, respectively. The dashed ovals seen in FIG. 3B mark the nanotubes in the membrane.

After comparing SEM images of the cell membranes subjected to various combinations of nanospearing conditions, it was seen that the microvilli in the membranes of the cells depicted in FIGS. 3A and 3B have the same site density, which is 15 microvilli/$\mu m^2$.

Figure 3C:
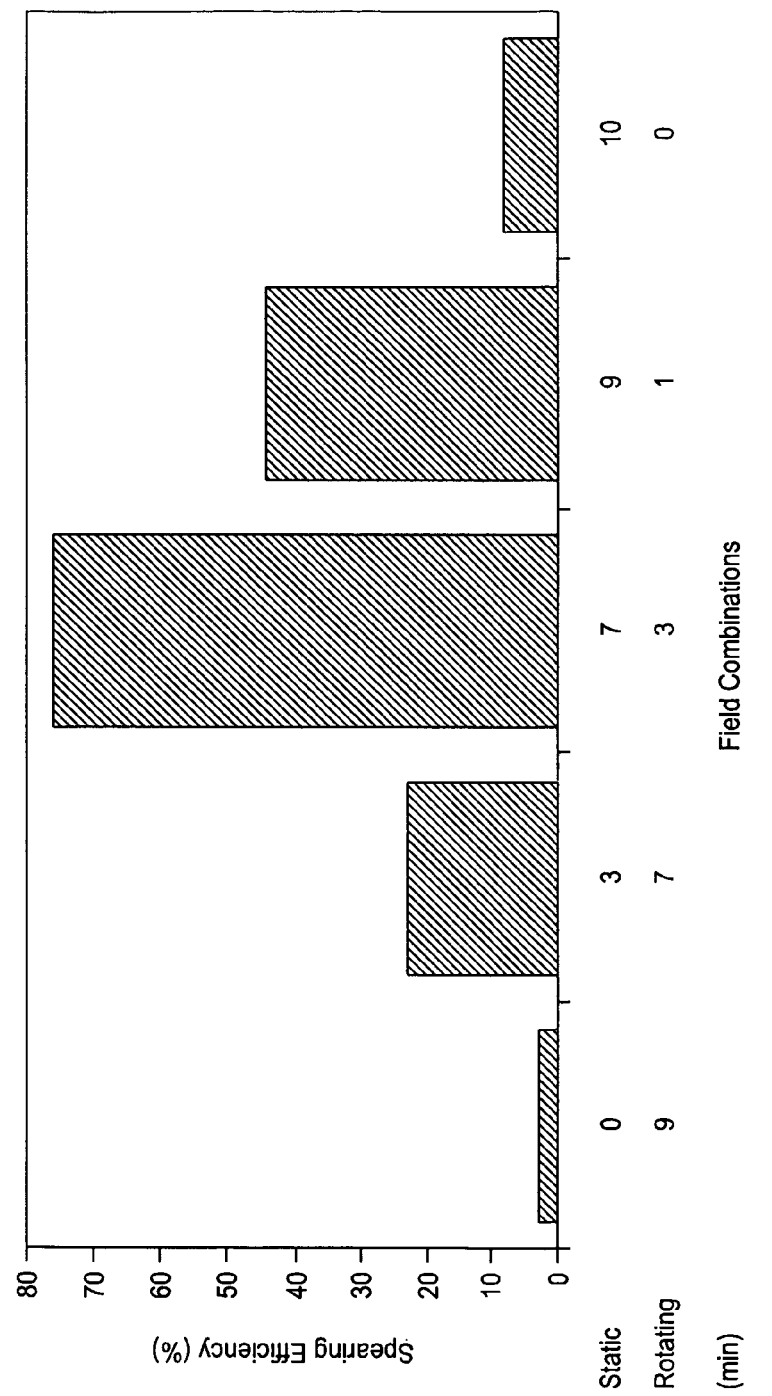
FIG. 3C illustrates spearing efficiency for various magnetic field combinations.

FIG. 3C illustrates the spearing efficiency of cellular membrane penetration for cells that were nanospeared under various magnetic field combinations. The process in which cells were subjected to spearing for three minutes in a rotating magnetic field and for seven minutes in a static magnetic field (this spearing process is denoted as "3-7" in this figure) resulted in greater nanotube embedding in the membrane (~76% of all cells) than the 10-0 or 0-10 combinations (i.e., lower than 10% of all cells). Thus, it is believed that nanospearing with a rotating magnetic field, combined with subsequent nanospearing with a static magnetic field, is more effective than nanospearing with only a rotating magnetic field and nanospearing with only a static magnetic field. It should also be noted that more than 90% of the MCF-7 cells remained viable after the combined rotating field spearing and static field spearing (i.e., the 3-7 spearing). These results were determined by trypan blue staining.

Figure 3D:
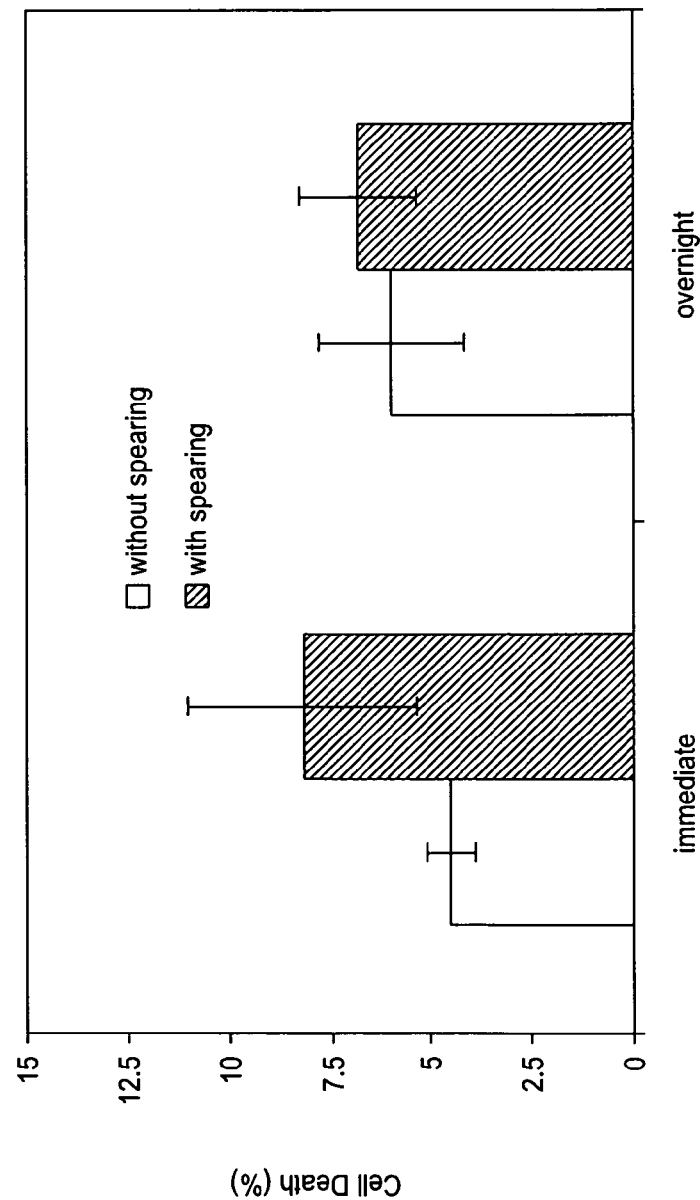
FIG. 3D illustrates immediate and overnight cell death data for cellular membrane penetration, with and without spearing.

Looking next at FIG. 3D, which illustrates the immediate and overnight cell death ratio for cellular membrane penetration with and without nanospearing, it can be seen that there is no significant difference in the cell death rates between the cells with nanospearing and those without nanospearing.

As shown in the above example, cellular membrane penetration by nanospearing opens a pathway for the nanotube to shuttle molecules into the target cells. Thus, with the passenger molecules secured to the nanotubes, effective biomolecular delivery can be conducted using the nanospearing techniques disclosed herein.

Example 3

Figure 4A:
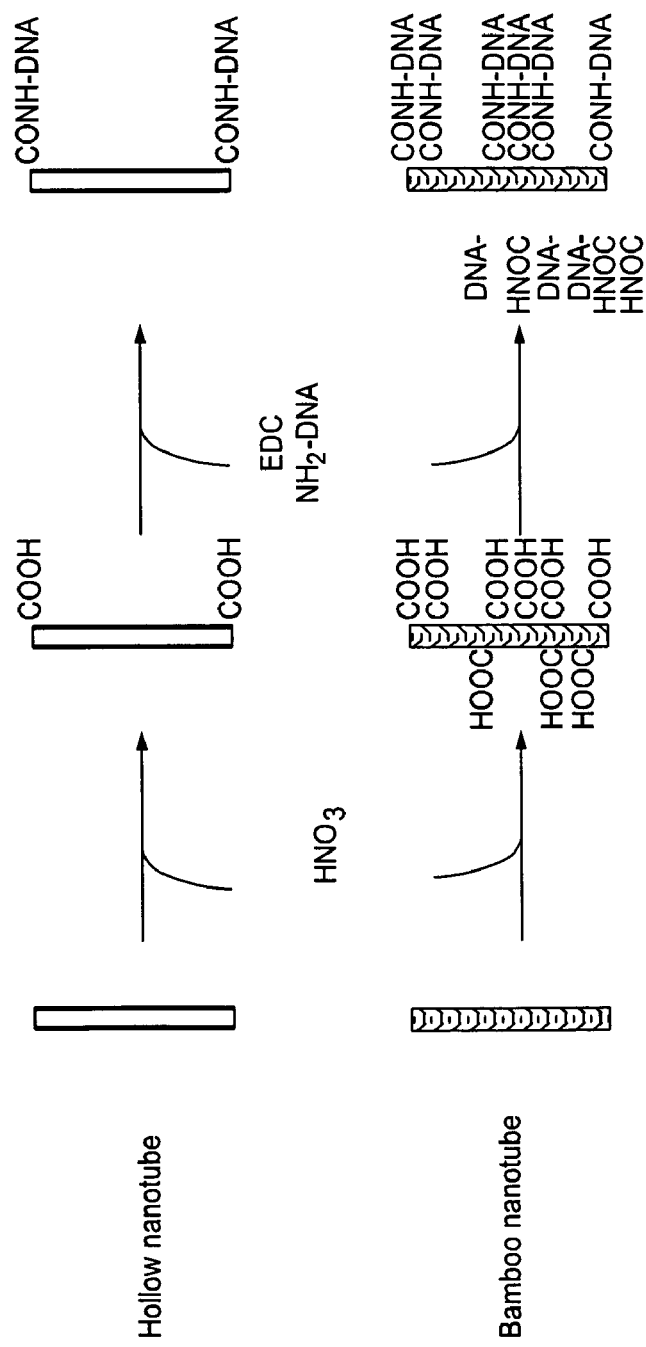
FIG. 4A illustrates DNA immobilization on several types of nanotubes.

In another example, the magnetically-drivable nanotubes were grown aligned on a 2×2 cm silicon wafer. Subsequently, they were scraped off and suspended in 5 ml of ethyl alcohol, resulting in an estimated concentration of approximately 1 pM. The suspension was then centrifuged at 10,000 g at room temperature for ten minutes. Next, the supernatant was discarded and the nanotubes were resuspended in 0.5 M $HNO_3$ to functionalize the nanotube surface with carboxyl groups, as shown in FIG. 4A. The container was then placed overnight near a Nd—Fe—B magnet.

Figure 4B:
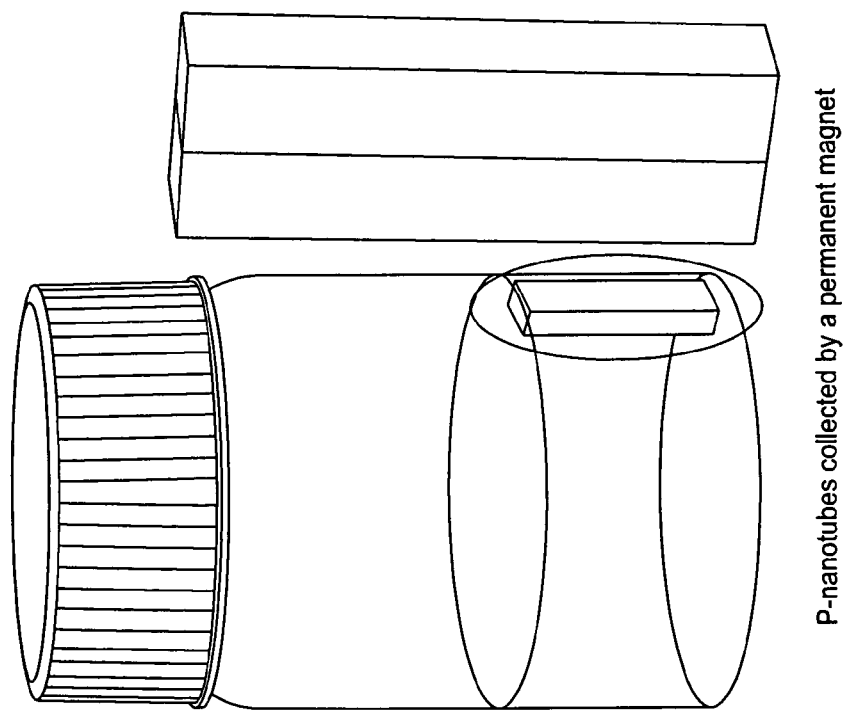
FIG. 4B illustrates the collection of p-nanotubes by a permanent magnet.

Looking next at FIG. 4B, the nanotubes are attached to the wall of the beaker closest to the magnet, as indicated by the red oval. The nanotubes were collected and washed three times with deionized water by repeating the centrifuge and resuspension cycle. These nanotubes were then stored in 5 ml of ethyl alcohol at room temperature.

The nanotubes extracted from 1 ml of the stock were mixed with 5 μg of plasmid and 10 mg of 1-ethyl-3-(3-dimethylaminopropyl) carbodiimide (EDC) in 0.1 M 2-[N-morpholino] ethane sulfonic acid (MES) buffer (pH 4.5) (as shown in FIG. 4A) for the aminization between the primary amine groups in the DNA molecules and carboxylic groups on the nanotubes. The reaction mixture was left in the dark at room temperature for one hour. The nanotubes were then precipitated by the same centrifugation conditions as above and resuspended in 1 ml of serum-free culture medium immediately before use.

As can also be seen in FIG. 4A, the bamboo-like nanotube is much more effective than the hollow nanotube at providing attachment sites for the biomolecules.

Figure 4C:
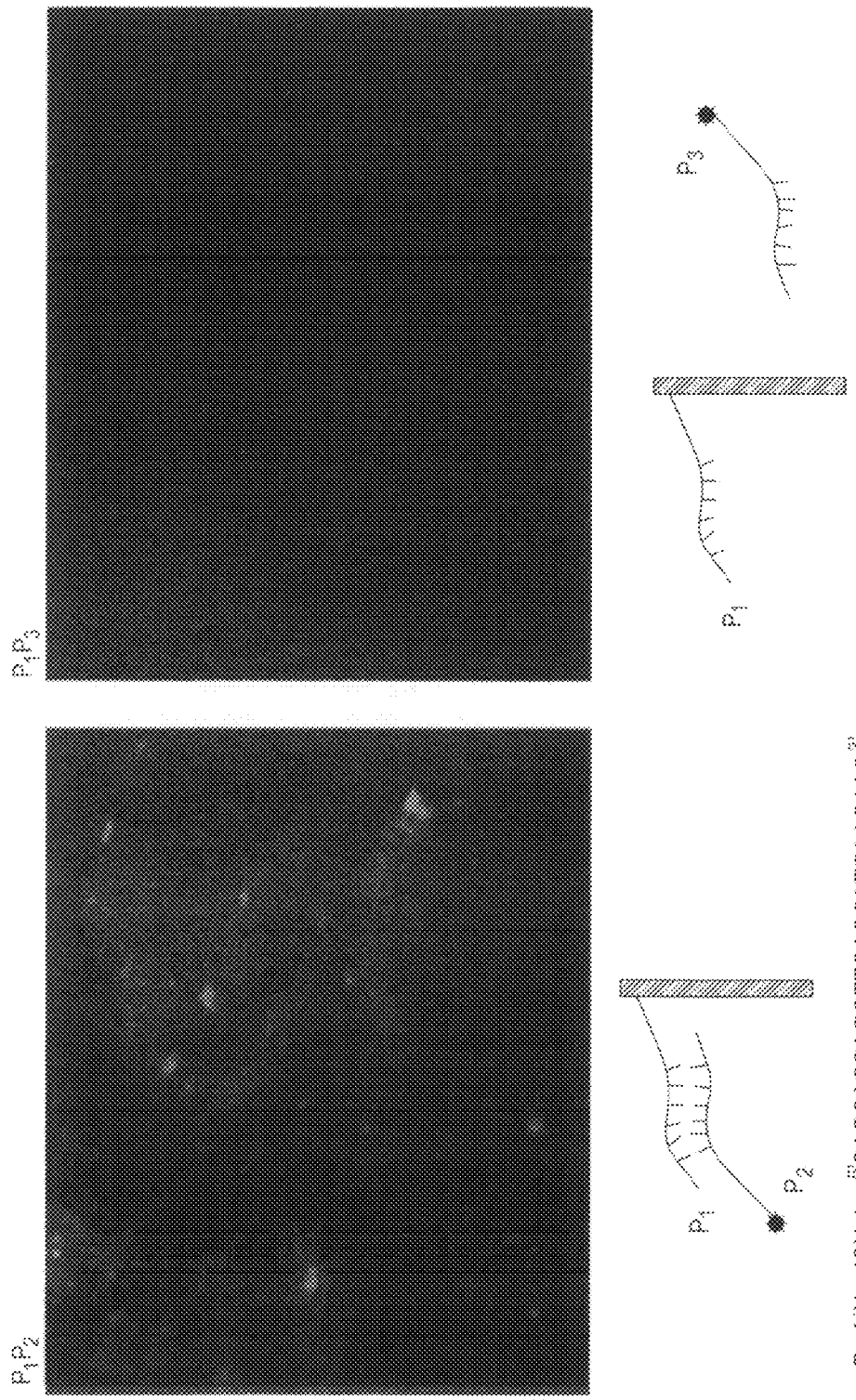
FIG. 4C illustrates DNA immobilization.

To visualize and test the immobilization, three oligoes ($P_1$, $P_2$, and $P_3$) were designed. The oligoes ($P_1$, $P_2$, and $P_3$) are shown in FIG. 4C and are listed in the Sequence Listing attached hereto, wherein $P_1$ is listed as SEQ ID NO:1, $P_2$ is listed as SEQ ID NO:2, and $P_3$ is listed as SEQ ID NO:3. In this case, $P_1$ was an amine, modified with a C6 arm at 5'; $P_2$ was designed to be a complementary pair of $P_1$, modified with a 5' FAM (6-carboxyfluroscein succinimidyl ester); and $P_3$ have a scrambled sequence that is not complimentary to $P_1$, but is modified with a FAM at 5'.

Immobilization was first conducted to affix $P_1$ onto the carbon nanotubes that had previously been functionalized with carboxyl groups. Then, the $P_1$-nanotube complexes were hybridized separately with $P_2$ and with $P_3$. As shown in FIG. 4C, a fluorescence signal was detected in the $P_1P_2$ sample, while none was observed in $P_1P_3$ sample. This observation shows (i) that $P_1$ is immobilized onto the nanotube, and (ii) that the ability of $P_1$ to recognize complimentary species is not damaged during the process.

In this same example, pEGFP-cl, the plasmid with the insert of enhanced green fluorescent protein (EGFP) sequence, was used to report the transfection, while the empty pcDNA3.1 vector was used as a negative control. Both pEGFP-cl and empty pcDNA3.1 were immobilized on nanotubes.

Example 4

Figure 5:
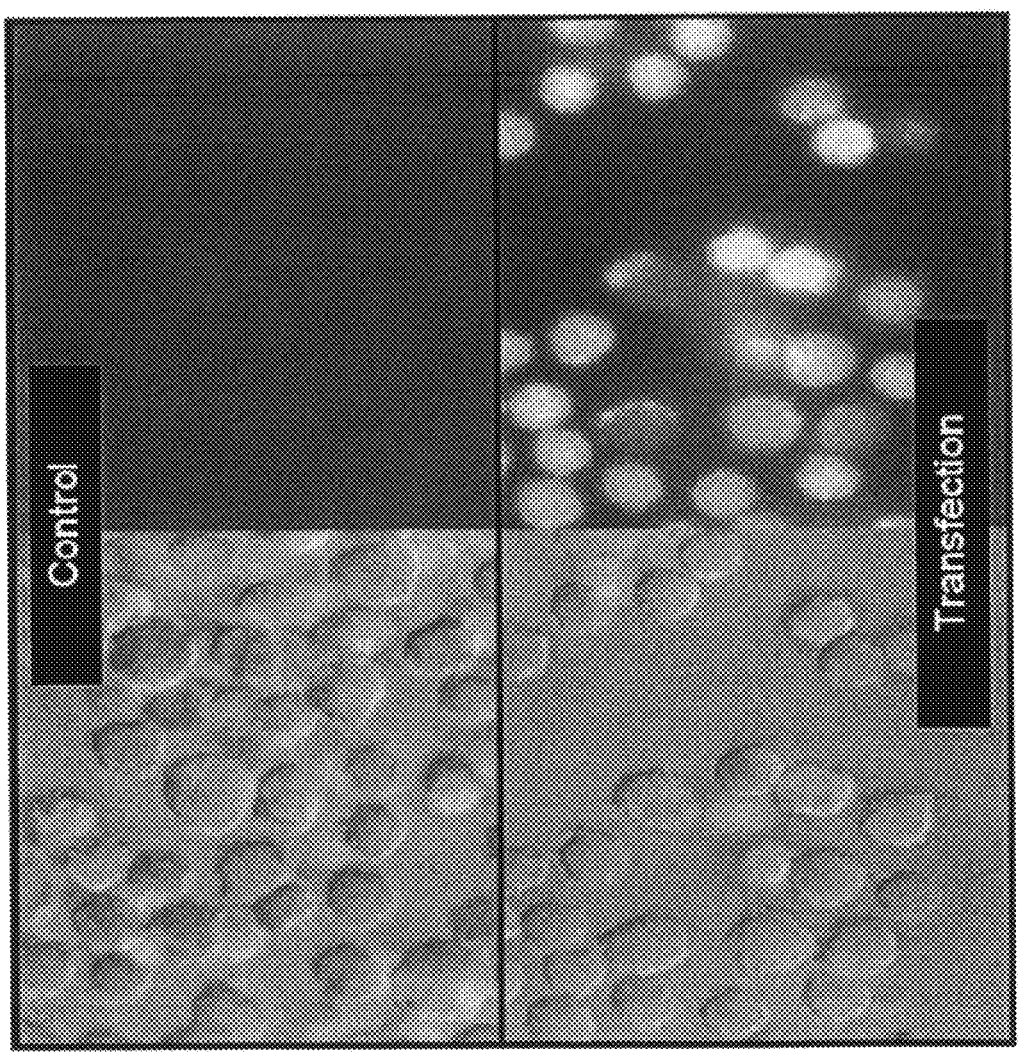
FIG. 5 illustrates transfection (with and without nanospearing) for Bal-17 cells.

In the following example, divisible cells, specifically Bal-17 (the mouse lymphoma B cell line) were transfected by the nanospearing technique in a manner similar to that described above. After nanospearing with the 3-7 protocol, (i.e., nanospearing for the period of 3 minutes in a rotating magnetic field and 7 minutes in a static magnetic field), Bal-17 cells were cultured for twenty-four hours. As a result, under a fluorescence microscope, approximately 100% of the Bal-17 cells had the EGFP in the transfection sample, whereas no detectable fluorescence was observed in the negative control Bal-17 cells (FIG. 5).

Figure 6:
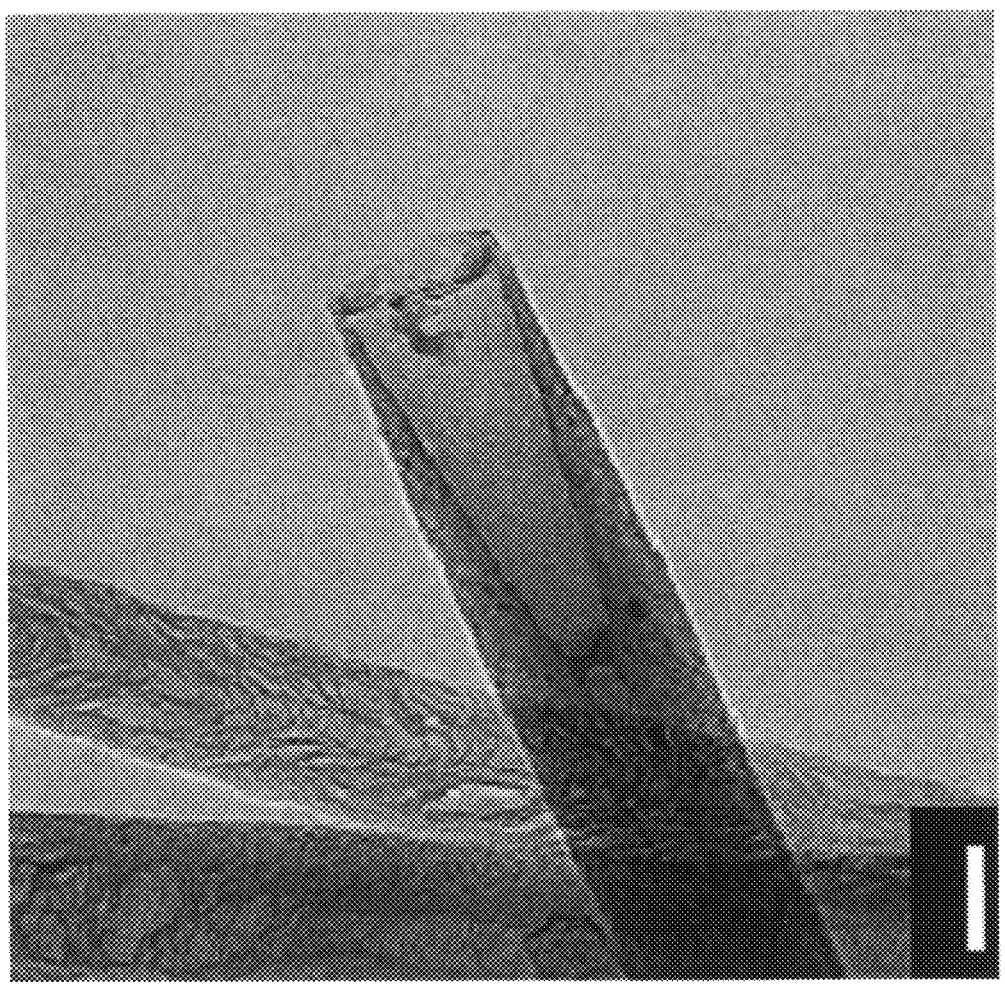
FIG. 6 shows transfection in a Bal-17 cell by nanospearing.

As shown in FIG. 6, where the scale bar marks are 50 nm, extreme oxidative conditions may be used to remove the magnetic metal particles from the nanotubes in accordance with a method well known to those skilled in the art. Thus, these nanotubes are not capable of being driven toward the cells using a magnetic field. In fact, the cells subjected to the 3-7 nanospearing protocol using the magnetic metal-free nanotubes had no fluorescence signal. In this case, the incubation (rather than nanospearing) of the cells with the plasmid-immobilized normal nanotubes (with nickel) did not produce any transfection.

Significantly, no signal was observed upon subjecting cells to the magnetic treatment in the presence of DNA plasmids only. These results indicate that the magnetic actuation of the nanotubes is important in order to achieve gene expression. Under these experimental conditions, the uptake pathway is not as efficient as the transfection mechanism.

The effectiveness of each of the two nanospearing steps, i.e., first using the rotating magnetic field and thereafter using the static magnetic field, can be evaluated in terms of the transfection by two protocols: (i) 15 minutes of exposure to a rotating magnetic field and 0 minutes of exposure to a static magnetic field (i.e., nanospearing with the 15-0 protocol); and (ii) 0 minutes of exposure to a rotating magnetic field and 15 minutes of exposure to a static magnetic field (i.e., nanospearing with the 0-15 protocol). Cells exposed to either of these procedures had low levels of fluorescence signals. In fact, the fluorescence signals in those procedures were barely above the background. This suggests the desirability of the aforementioned two-step nanospearing protocol for efficient transfection.

Example 5

In the following example, an ex vivo splenic B cell was used to show the efficiency of transfection in a non-dividing cell using the nanospearing techniques described above. As stated above, non-dividing cells are generally difficult to transfect using conventional transfection techniques.

Figure 7B:
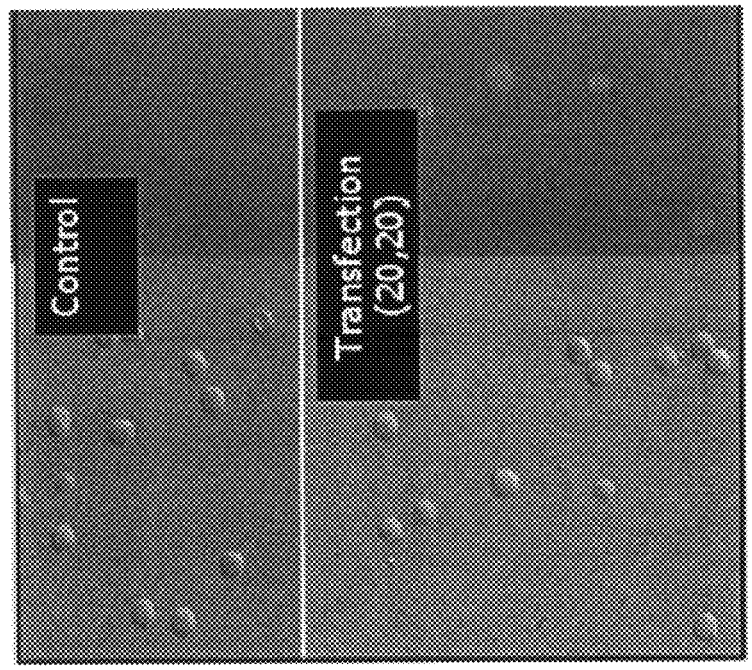
FIGS. 7A and 7B illustrate ex vivo transfection in B cells.
Figure 7A:
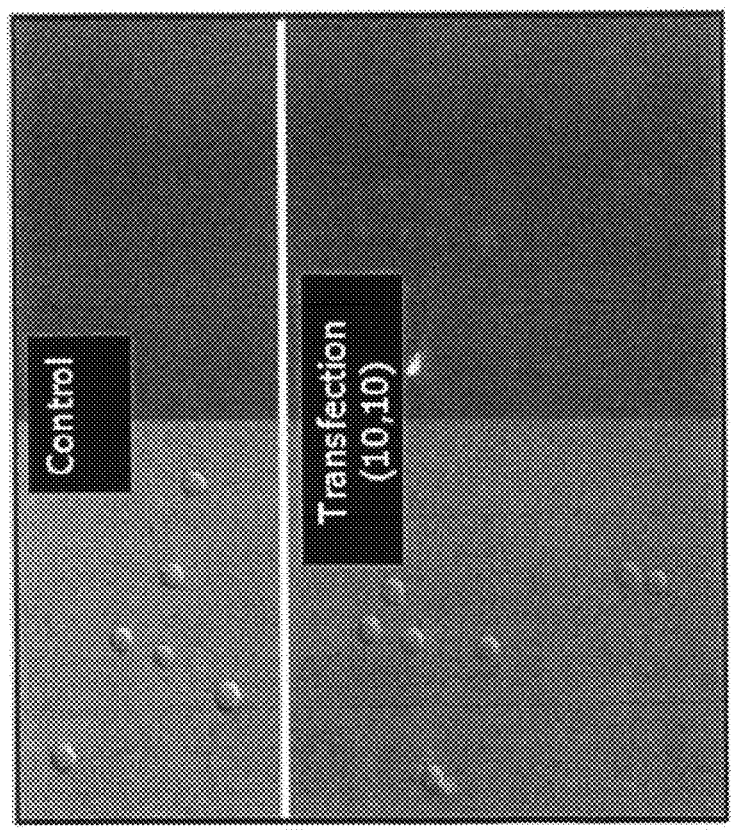
Figure 7C:
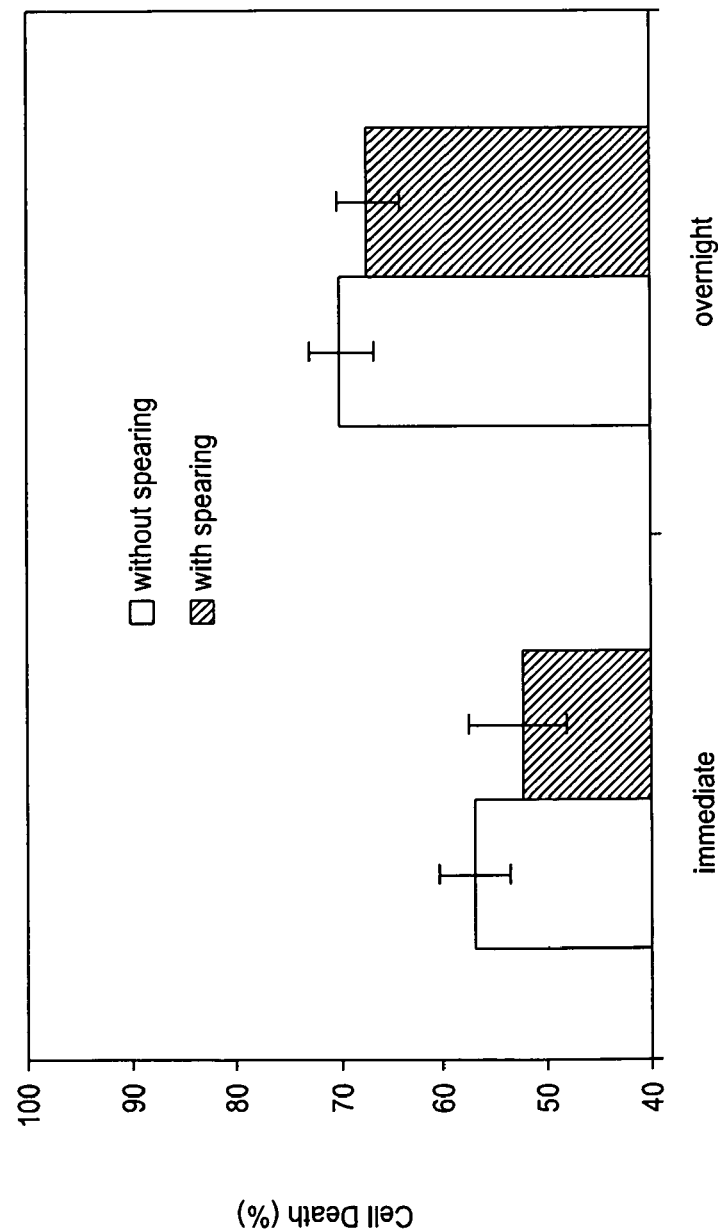
FIG. 7C illustrates immediate and overnight cell death data for transfection with and without spearing for ex vivo splenic B cells.

More particularly, the mouse splenic B cells were first purified from Bal b/c mice and cultured in accordance with techniques well known to those skilled in the art. Using fluorescence microscopy to observe the results, it was shown that almost 100% of the primary B cells express EGFP within twenty-four hours after the nanospearing, and the amount of fluorescence increased with the spearing time (compare FIG. 7B and FIG. 7A). Notably, even with the longest spearing time (i.e., the 20-20 protocol), which corresponds to 20 minutes of spearing under the rotating magnetic field and 20 minutes of spearing under the static magnetic field), there was no obvious decrease in cell viability (as compared to the viability of cells subjected to the same procedures in a nanotube-free medium), as determined by trypan blue staining (see FIG. 7C).

Example 6

In the following example, primary cortical neurons were used to show the efficiency of transfection using the nanospearing technique described above in non-dividing cells.

Figure 8B:
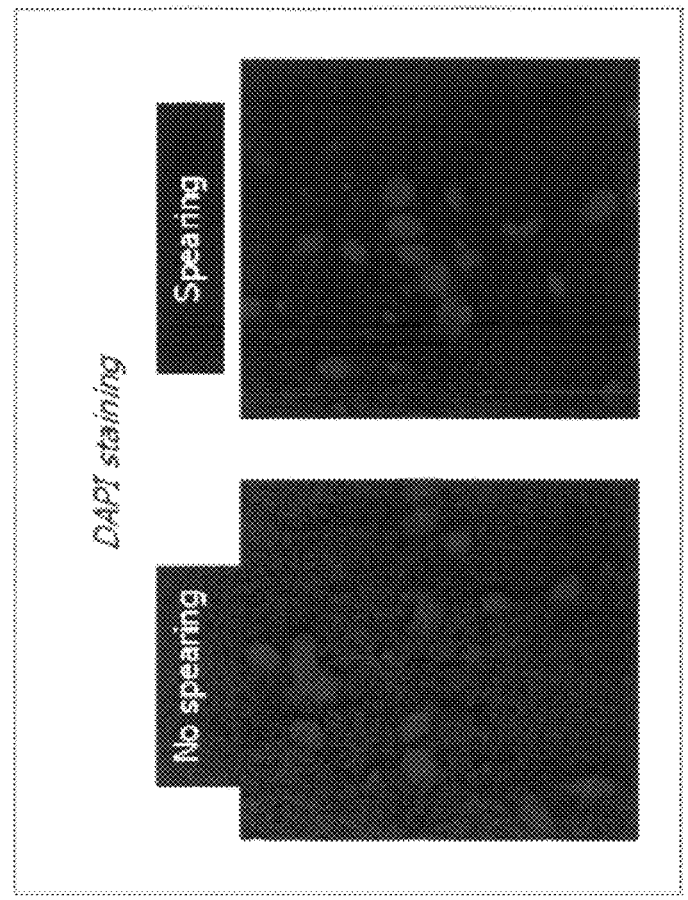
FIGS. 8A and 8B show transfection in primary cortical neurons.
Figure 8A:
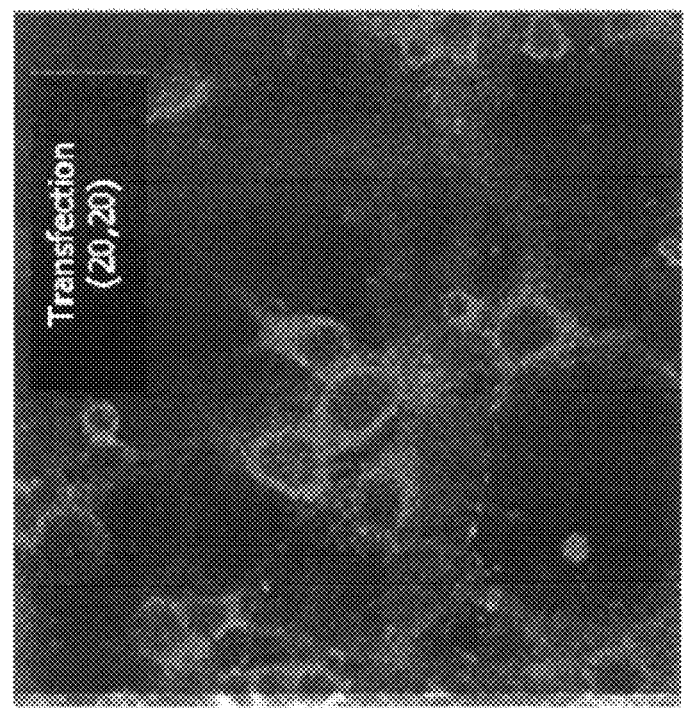

More particularly, the cortical neurons were first separated from embryonic C57/BL6 mice. The nanospearing protocols applied in this example were 10-10 (which corresponds to 10 minutes under the rotating magnetic field and 10 minutes under the static magnetic field), 15-15 (which corresponds to 15 minutes under the rotating magnetic field and 15 minutes under the static magnetic field), and 20-20 (which corresponds to 20 minutes under the rotating magnetic field and 20 minutes under the static magnetic field). Even after twenty-four hours, no fluorescence was observed. After forty-eight hours in culture, the neurons subjected to the 20-20 spearing condition had green fluorescence (see FIG. 8A). As determined by fluorescence microscopy, the percentage of green cells was approximately 80%. Process retraction was noticed in all neurons subjected to all nanospearing conditions at twenty-four hours. The neurons typically return to normal after forty-eight hours. Nucleic staining with 0.5 μg/ml 4,6-diamidino-2-phenylindole (DAPI) showed a similar cell density in the control and nanospeared groups even up to seventy-two hours (see FIG. 8B). This experiment suggests that nanotube spearing can perturb cells, but that this perturbation is small enough for the neurons to recover from the perturbation within a short period of time. The exogenous gene was expressed after the recovery in forty-eight hours.

ADDITIONAL ASPECTS OF THE INVENTION

Nanotube Movement. The response of a suspension of magnetizable metal filled carbon nanotubes to magnetic stimulation was demonstrated by placing the suspension on a magnetic stir plate, without a magnetic stirring bar in the container. When the nanotubes could be magnetically driven, an optical "flashing" effect was observed, which is synchronized with the rotating magnetic field. Observations using electron microscopy determined that magnetically drivable nanotubes are generally short (<2 μm) and contain an elongated magnetic metal particle with the aspect ratio (the ratio of length to width)>3.

In the rotating magnetic field of the stir plate, the nanotubes containing elongated nanoparticles may oscillate, or spin around an axis perpendicular to their length, as they try to align with the rotating magnet. The "flashing" effect may be due to the temporary increased transparency of the solution, when the aligned nanotubes face the observer for a short time during their spinning motion. This was observed using a stroboscope, and it was confirmed that the spinning frequency of the magnet is related to the "flashing" frequency. This experiment suggests that the "flashing" effect was due to nanotubes spinning in place, as opposed to a cloud of nanotubes following the edges of the spinning magnet, which we would expect at low rotation speeds only.

Our analysis of the drivable nanotubes in the field of a moving bar magnet of a stir plate shows that they behave as follows. For any velocity v below a critical velocity $v_c$ (e.g., $v<v_c$), the nanotubes will align and follow the motion of the magnet. Experimentally we find that $v_c$ is very small, and difficult to achieve with a magnetic stir plate. For $v>v_c$, the nanotubes lag behind the rotating magnet, and may begin to oscillate or spin, generally aligning lengthwise with the direction of the spinning magnetic field. In addition, they may develop a jigsaw-like, pulsing motion, anytime the magnet passes by. We hypothesize that first, a nanotube is accelerated in the opposite direction to the incoming magnet (towards the field gradient near the first edge), then stops briefly between the edges of the magnet, and then it is accelerated in the direction of the moving magnet (towards the field gradient near the second edge). Thus each pass of the magnet could produce 2 jiggle-like movements of the forward-moving nanotube, at higher speed at higher magnet rotation, that can improve the nanospearing efficiency. The direction of the jiggles may depend in a complicated way on the nanotube initial position (relative to the magnet), orientation, fluid viscosity, magnet shape, speed, etc.

The jiggle motion of the nanotubes (in the first step of the two-step protocol using rotating and static magnetic fields) is characterized by two parameters: the jiggle amplitude (i.e., displacement) and frequency. In the rotating magnet agitation scheme, increasing the frequency should reduce their amplitude. It is expected, that an optimal value of this speed $v_2$ exists that maximizes the cell penetration, and assures minimal damage to the cell.

Alignment Of Nanospears. The behavior of the these nanotubes can be explained in terms of motion of the magnetic nanoparticle, responding as a magnetic dipole to an external magnetic field of the rotating, permanent magnet of the stirrer. The response is twofold. First, it is aligned, in response to a torque N given by Eq. (1)

$$N = m \times B \quad (1)$$

where B is the magnetic field, and m is the magnetic dipole moment of a nanoparticle. For non-elongated (e.g., spherical) nanoparticles, the induced dipole m will be parallel to B, and therefore N=0. In this case, the nanoparticle (and therefore also the entire nanotube) is not affected by the magnetic field, i.e., does not turn to align with B, because the dipole is already aligned. In the case of the elongated nanoparticles that are used in accordance with the present invention, the dipole moment m may not be parallel to B. Then the torque, N, is nonzero, and therefore the elongated nanoparticle and its associated nanotube turns to align with the field. Therefore, for alignment to occur, the nanotubes must contain these elongated nanoparticles.

Driving Of Nanospears. The second kind of response of a dipole to the magnetic field is the translational motion along its axis, in response to the force given by $$F = m \nabla B \quad (2)$$

where m and B are amplitudes of the nanoparticle dipole moment and the magnetic field, respectively. This causes translational motion of the nanotube, mostly along its length as this minimizes the friction forces. In contrast to the spinning motion, which occurs only for the nanotubes with elongated metal particles, the translational force will occur for all nanoparticles, spherical and elongated alike.

Methods For Controlling Nanotube Motion And Alignment. There is a considerable control of the nanotube motion in a magnetic field, since there are two independent degrees of freedom available. The magnetic field itself controls the nanotube orientation (steering), and the field gradient controls its acceleration (driving). Since the magnetic field and its gradient can be oriented in different directions, the nanotube orientation and its acceleration can be made, but do not have to be parallel. This can be controlled by the design, and the motion (dynamics) of the magnetic actuation. In the case of the magnetic stirrer discussed above, B is not, for most of the driving cycle and in most of the volume of the container, parallel to $\Delta B$. Therefore, the field orientation is sub-optimal, but is nonetheless sufficient to achieve efficient nanospearing.

A better design, which may eliminate one of the steps in the protocol, can be achieved through rational design of the system. In one implementation, the design consists of a high-speed motor, a high field magnetic rotor, and a cuvette, which optimizes the nanotube actuation. In this design, the rotor contains a permanent magnet which produces magnetic field perpendicular to the rotor axis of rotation. The cuvette sits outside of the rotor, so the field gradient is always nearly parallel to the field itself. The nanospearing strength is then tunable by the motor speed, processing time, and the concentration of nanotubes per cell.

Since cells are generally much bigger, heavier, and less magnetic than the nanovehicles, they are relatively stationary in suspension. Each cell is then speared by a number of nanotubes, which are aligned and driven by the rotating magnet. In such an implementation, several million cells could be speared simultanteously.

Another design that may simplify the protocol utilizes only the second step of the two-step nanospearing protocol (i.e., orientationg and driving with the static magnetic field). In the examples, the use of second step alone (i.e., the application of a permanent magnet) caused nanospearing, but it was inefficient when compared to two-step protocols. An improvement to this step would use an electromagnet, instead a moving permanent magnet, to generate temporal magnetic pulses. During each pulse, the nanotubes will first align parallel to the magnetic field, and then be accelerated towards the gradient of the field, which in this case can be made exactly parallel to the field itself. A properly designed actuation head can maximize the amplitude of ΔB. By applying the pulse repeatedly, a jigsaw motion of a nanotube can be created, which should penetrate membranes of cells placed in its way.

Additional Constructions

As described above, a magnetic field having a gradient, orients and drives the nanotubes in a medium toward target cells which are immobilized in the medium (e.g., cultured on a substrate). After preliminary spearing (which is effected by moving the nanotubes in the magnetic field), the target cells are transferred to culture dishes containing a nanotube-free medium so as to enhance spearing by the static field of a permanent magnet.

In order to increase the throughput of transfection, a novel GeneBlender apparatus is disclosed to provide a rotating magnetic field, and a novel GeneHammer apparatus is disclosed to provide a static field.

Figure 9:
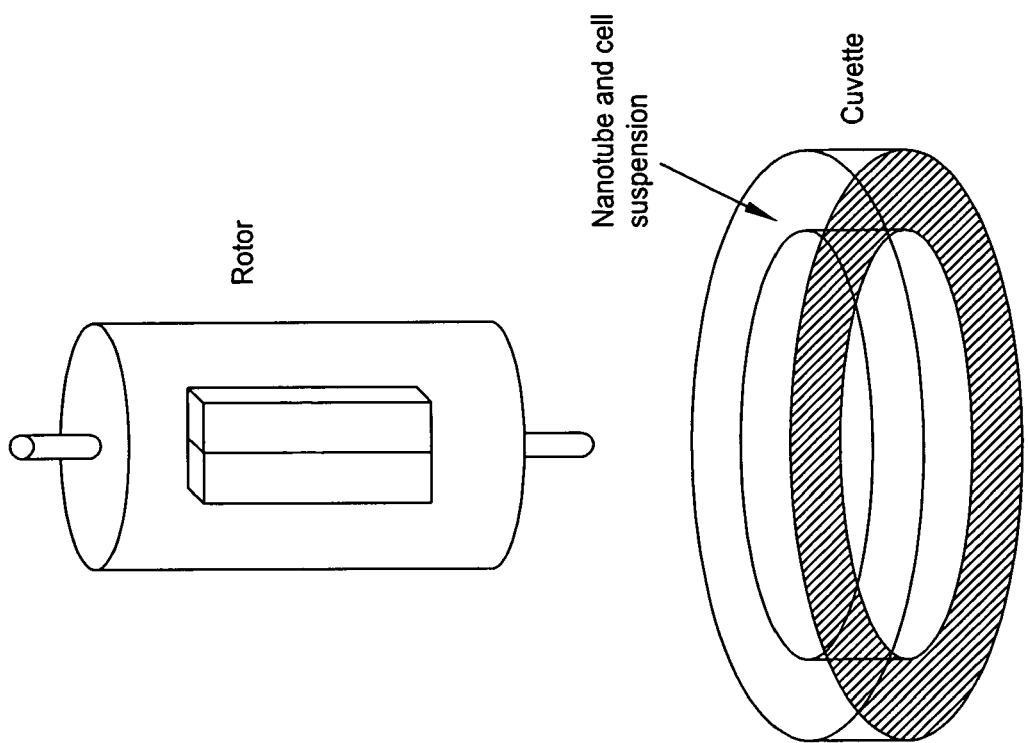
FIG. 9 illustrates the GeneBlender apparatus comprising a high speed motor, a magnetic rotor, and a special cuvette.

More particularly, the novel GeneBlender apparatus provides a rotating magnetic field that actuates nanotubes at a high spearing velocity. In one embodiment of the present invention, the GeneBlender apparatus comprises a high speed motor, a magnetic rotor, and a special cuvette (see FIG. 9). The cuvette has its containing space around the rotor and receives the target cells, which are not fixed to a substrate. More particularly, because target cells have a larger volume and a larger mass than nanotubes, the target cells can be considered stationary objects in suspension during the spearing process. Each target cell can potentially be speared by a number of nanotubes located nearby in the suspension. Therefore, millions of target cells in the cuvette can be speared simultaneously by the moving nanotubes. The spearing strength of the GeneBlender apparatus can be adjusted by changing the motor speed, the duration of magnetic spearing, the diameter of the cuvette, the concentration of nanotubes relative to the concentration of cells, etc.

Figure 10:
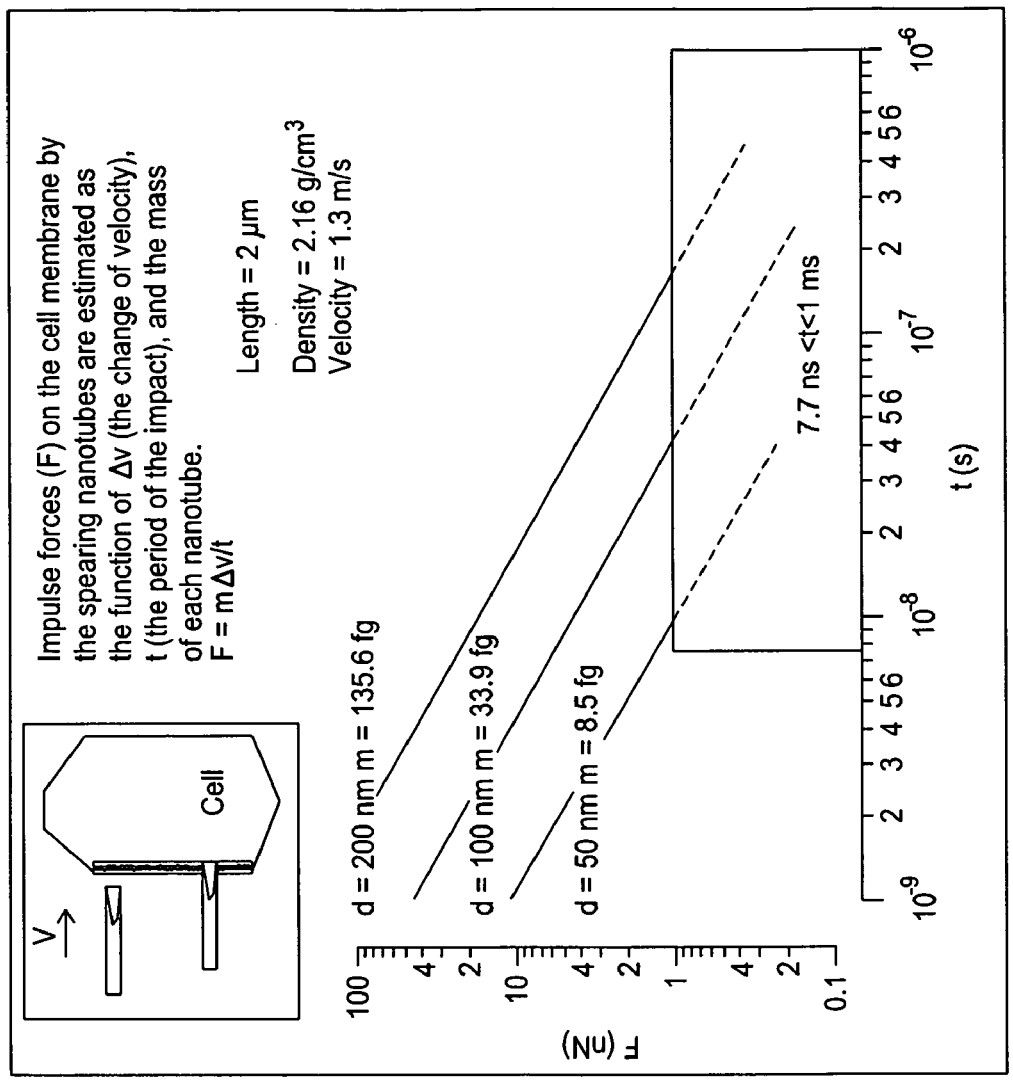
FIG. 10 illustrates prior art cell membrane penetration by a Si nanoneedle attached on an AFM tip, and penetration of cells by nanotubes of various diameters.
Figure 10:
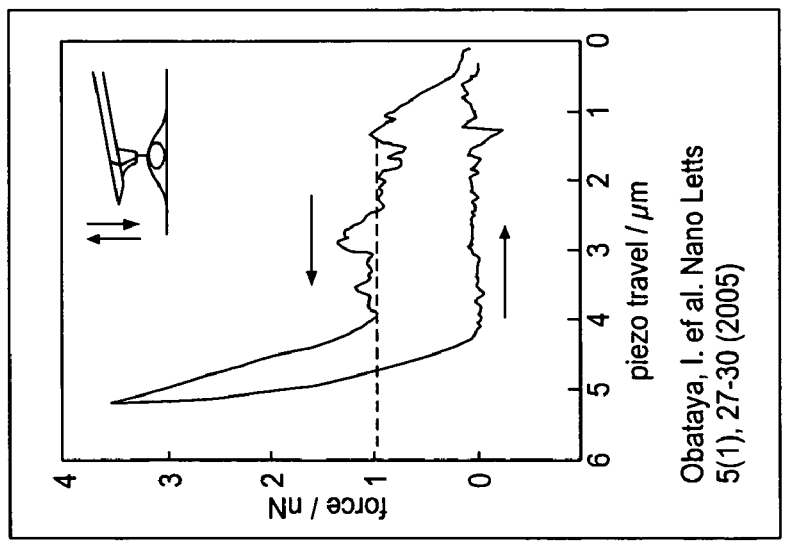

A simplified model describing the GeneBlender nanotube spearing process (i.e., the first step in the two step nanospearing process) is shown in FIG. 10. The nanotubes move in a direction which follows the rotation of the stirrer magnet and collide with the effectively stationary cells. The momentum of the moving nanotube can generate an impact force F on the cell membrane. This force F is a function of Δv (the change in velocity), Δt (the period of the impact), and the mass of each nanotube (m). This force can be expressed as:

$$F = m \cdot \Delta v / \Delta t \quad (3)$$

It has been previously reported that the membrane of a cell may be penetrated by a Si nanoneedle attached on an AFM tip. See FIG. 10. It was found that a 1 nN force was required for successful membrane penetration by the needle. Applying Equation (3), it can be determined that nanotubes of three typical sizes (i.e., 50 nm, 100 nm, and 200 nm) are able to generate a force larger than 1 nN within the estimated impact period t, where 7.7 ns<t<1 ms.

In reality, a spearing nanotube is subjected to several different forces. Primarily, these forces are the magnetic force $F_m$ and the frictional force $F_f$, which are expressed as:

$$F_m = \mu \frac{\partial B}{\partial z} \quad (4)$$

$$F_f = f_0 \cdot \frac{(2/3)^{1/3} \cdot P^{2/3}}{\ln(2P) - 0.30} \cdot V \quad (5)$$

where P=a/b, $f_0 = 6\pi\eta R_0$, $$R_0^3 = \frac{3ab^2}{2},$$

η is the viscosity of the medium, V is the velocity of the nanotube, a is the length of the nanotube, and b is the diameter of the nanotube.

As $F_f$ is proportional to the velocity, there should be an upper speed limit for the nanotubes to move while following the path of a magnetic field and its gradient. This is the point where $F_m$ is cancelled by $F_f$. Apparently, in order for the spearing speed to reach a higher level, a stronger magnetic field gradient and a high speed motor is necessary to drive the nanotubes.

Figure 11:
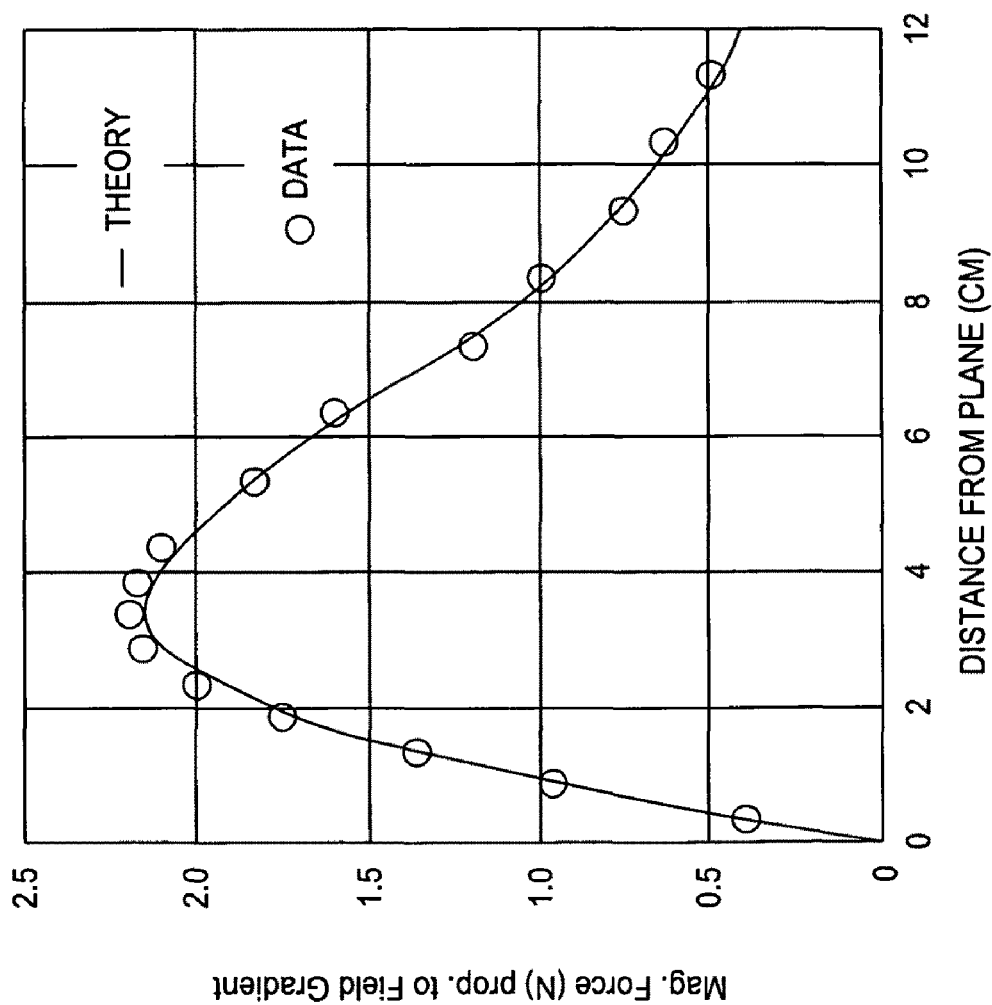
FIG. 11 illustrates normal magnetic field gradient distribution.

It should be appreciated that the magnetic field gradient normally distributes differently than the field strength. As shown in FIG. 11, the axial magnetic field gradient of a single current-carrying loop demonstrates a bi-phase distribution versus the distance from the loop plane. The maximum gradient can be found at a distance away from the plane, where the flux density is the highest. Therefore, the gradient distribution of the magnetic rotor in the GeneBlender construction is such that the point where the nanotubes gain the most velocity is located at a specific distance to the magnet surface. Thus, the radius of the cell cuvette is determined by the foregoing analysis.

Figure 12:
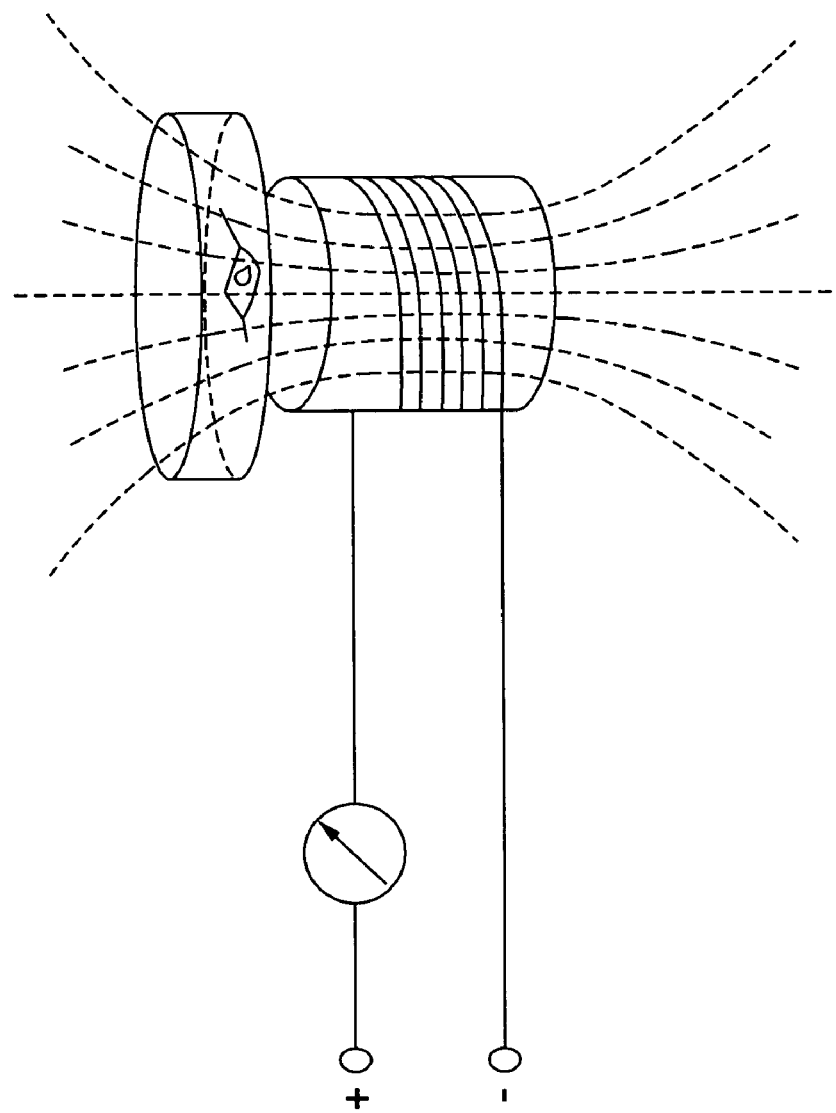
FIG. 12 illustrates an electromagnet used to generate temporal magnetic pulses.

In another alternative embodiment of the present invention, the GeneHammer apparatus is provided to generate a static field for the second step in the nanospearing procedure. In general, the GeneHammer receives the target cells (initially speared by the nanotubes) and establishes a pulsed static field so as to progressively set the nanotubes further into the target cells. More particularly, looking now at FIG. 12, an electromagnet is used to generate temporal magnetic pulses. During each pulse, the nanotubes are aligned with the field and pulled into the target cells. By applying the pulse repeatedly, nanotubes penetrate cell membranes in the manner similar to how a hammer drives nails into a surface. The apparatus comprises no moving part, yet provides a well regulated pull direction and pull force. As a result, by applying magnetic pulses with carefully chosen properties (i.e., frequency, strength, etc.), the nanotubes may be "hammered" in to the target cells to a desired degree.

Figure 13:
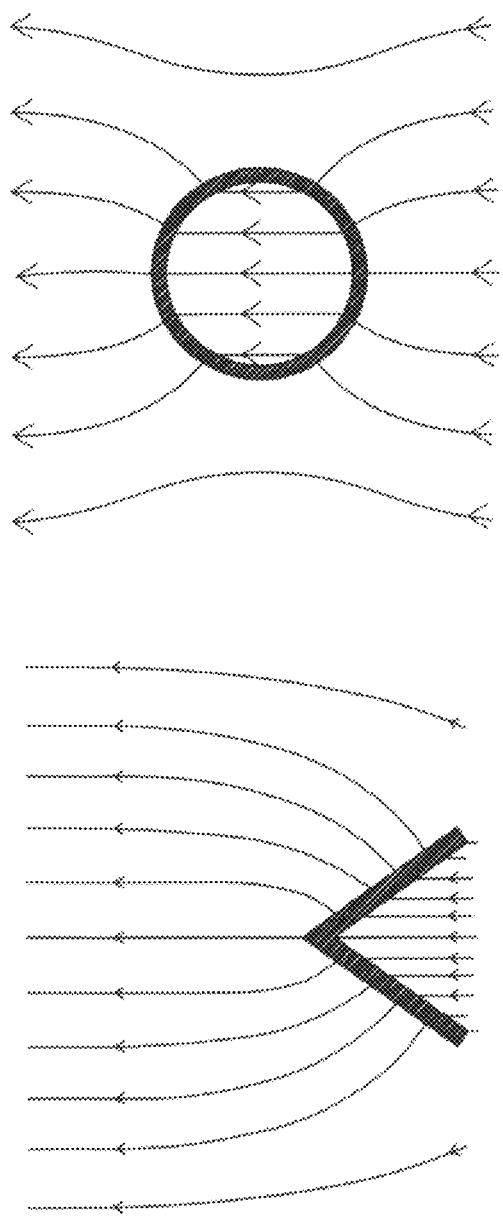
FIG. 13 illustrates some typical patterns of local magnetic fields.

An adapter made of soft magnetic materials with high permeability, such as iron, is placed between the culture dish and the face of the electromagnet. Structures are preferably machined in its top surface in order to enhance the local magnetic field gradient. Some typical patterns of local magnetic fields are shown in FIG. 13. The structure geometry can be optimized according to an analysis of the desired magnetic field. The distance from the magnet face to the point with the highest gradient can be determined as well; this is the point at which the cells are set from the magnet face.

In the alternative embodiment of the present invention, the GeneHammer apparatus can be modified for different uses. More particularly, if the applied magnetic force is strong enough, and the cells are cultured on a suspended mesh-like substrate, the nanotube spear can be used to "fish" intracellular molecules, such as mRNA or other nucleic acids. The nanotubes penetrate through the cell body and pull out target molecules corresponding to the pre-attached bio-probes.

It should be appreciated that the size of the GeneHammer magnet can be enlarged for spearing a large quantity of cells. Alternatively, the size of the magnet can be reduced for high throughput transfection. By way of example but not limitation, the array can be designed to match a 96-well culture plate so that scientists can perform various transfections or tests simultaneously under different conditions.

The use of the GeneHammer apparatus is not limited to in vitro applications. By way of example but not limitation, the nanotube spear can be injected into living cancer tissue. The GeneHammer apparatus may also be used outside the tissue so as to actuate nanotubes to spear cells and/or deliver drugs. Such an application could also be used for human or animal vaccinations.

In one preferred construction of the GeneHammer apparatus, an LC circuit is used in combination with a solid state relay and high rated diodes. The electricity in the LC circuit may be used to drive the coil so as to produce magnetic pulses with the desired properties. For example, by choosing appropriate values in the LC circuit, a 2.5 ms magnetic pulse can be generated.

The magnetic influx can be estimated based on the relationships stated by the equations:

$$B = \mu NI$$

$$L = \mu N^2 A/l$$

where B is the magnetic influx, L is the inductance, μ is the magnetic permeability of the media in the center of the selenoid, N is the number of the coils, A and l are the cross-section area and the length of the solenoid, respectively, and I is the current through the coil.

Combining these two formulas together yields:

$$B = LII/NA$$

For example, where L is 0.0025 Henry, l is 1 cm, I is 150 Amperes, N is 270, and A is 3.2 cm², then the influx at the center of the selenoid is 43133 Gauss.

The distribution of magnetic flux along the selenoid axis is plotted versus the distance to the coil face. It has been found that the magnetic field drops quickly. It is not difficult to produce a 6000 Gauss field, which is equivalent to that of the permanent magnet for the second nanospearing step described above, using this design.

Discussion

As exemplified above, the present invention provides a method for highly efficient delivery of biomolecules (e.g., plasmids or other nucleic acids) into ex vivo neurons, splenic B cells, transformed mouse B lymphocytes, and other kinds of cells and tissues. By comparison, EGFP expression is not detectable when Lipofectamine 2000 is used as a vehicle for transfection in both Bal-17 cells and ex vivo splenic B cells.

A series of experiments carried out in various conditions illustrate various mechanisms of the nanospearing-mediated transfection. The results of these experiments are summarized in FIG. 9. The experiments demonstrate that, in order to achieve an efficient transfection in the nanospearing experiments, three aspects are important:

(i) providing magnetically-responsive nanotubes with their "passenger" biomolecules (e.g., plasmids or other nucleic acids);

(ii) providing an appropriate magnetic field having a gradient; and (iii) orienting and driving the nanotubes with the magnetic field and its gradient.

The incubation experiment clearly excludes the involvement of plasmid uptake by biopathways such as through endocytosis and pinocytosis. Therefore, these results strongly suggest that the mechanical penetration of cell membranes is through the mechanism of the nanospearing mediated molecular delivery. Because of the nanoscale of this mechanical impact, the penetration makes only a minor perturbation in cells. Therefore, the viability of cells (even those as vulnerable as primary neurons) remains substantially unchanged after the nanospearing.

As discussed above, the expression of exogenous genes in B cells and neurons represents significant challenges to researchers, with the greatest challenge being the low efficiency of transfection. This invention solves this problem, and is believed to be particularly useful for those cells and tissues which are poorly transducible. In fact, during testing, the nanospearing technique of the present invention was found to be much more efficient than many proprietary products (e.g., amaxa's Nucleofector) in mediating non-viral transfection in primary cells.

Although the present disclosure focuses on the delivery of plasmid DNA, the nanospearing techniques can also be applied to transport other macromolecules, such as proteins or peptides and RNAi conjugates, into mammalian and non-mammalian cells, so as to exploit the intensively studied surface chemistry for immobilizations.

The nanospearing procedure of the present invention may also be utilized for in vivo applications, such as gene therapy and tissue engineering.

It should be appreciated that carbon nanotubes can facilitate the delivery of macromolecules in several ways. It has been demonstrated that carbon nanotubes can be internalized by the cell, although the mechanism of this process is still unknown. Similarly, researchers have observed the cellular uptake of nanotubes by the endocytosis pathway. In both these situations, the cells received appreciable signals of the immobilized molecules after incubation with a sufficient amount of carbon nanotubes (e.g., 1-5 μM). By way of comparison, the nanospearing technique only requires as little as 100 fM of nanotubes for almost ideal transfection efficiency. Hence, the use of magnetic force to orient and drive magnetically-responsive nanotubes, as disclosed in the present invention, results in $10^7$-fold improvement in the molecular shuttling efficiency. The magnetic force-mediated cell penetration may provide a convenient targetable gene delivery approach, in parallel to a method in which cells are pinned on an array of nanotube bundles with attached plasmids.

In addition, it has been recently demonstrated that a cell plasma membrane and nucleus may be penetrated by a silicon nanoneedle attached to an atomic force microscopy tip. In another aspect of the present invention, the delivery of macromolecules to a single targeted cell can also be effected using this single nanoneedle spearing. However, this method is a low throughput process, so that it may not be suitable for supporting biochemical assays with a large quantity of cells.

The nanospearing technique of the present invention can be optimized to reduce the amount of DNA required for each transfection. In the experiments conducted in accordance with the present invention, the DNA plasmid can be used at saturating concentration, which is about $10^3$ times higher than that of the nanotubes. Future quantitative assays of the nanotube functionalization and plasmid immobilization may help reduce plasmids consumption without affecting the transfection efficiency.

Using the nanospearing technique of the present invention, very effective gene delivery may be achieved with both dividing and non-dividing cells. The non-dividing cells (e.g., primary B cells and neurons) are notoriously hard to transfect, and have been effectively transfected in the past only by viral vectors. Nanospearing, as a non-viral approach, yields a transfection efficiency equivalent to that of the viral approaches, while avoiding the disadvantages associated with viral approaches. The present invention immediately benefits in vitro gene delivery for overexpression and knockdown in a variety of cells. In the future, in vivo applications that are rarely possible using non-viral techniques, such as gene therapies, genetic vaccination, stem cell-based tissue engineering and drug delivery, may become possible using the nanospearing method of the present invention.

Further Modifications

The invention may be embodied in other specific forms without departing from the spirit or essential characteristics thereof. The present embodiments are therefore to be considered as illustrative and not restrictive, the scope of the invention being indicated by the appended claims rather than by the foregoing description, and all changes which come within the meaning and range of the equivalency of the claims are therefore intended to be embraced therein.

What is claimed is:

1. Apparatus for delivering molecules of biological interest to the interior of a cell, comprising:
   an elongated nanostructure comprising a distal end, a proximal end, and a longitudinal axis extending between the distal end and the proximal end;
   magnetic material carried by the nanostructure, the magnetic material being configured such that, when the nanostructure is positioned within an appropriate magnetic field having a gradient, the nanostructure will be oriented and driven, distal end first, in a first direction; and
   regions formed on the nanostructure which are configured to bind the molecules thereto;
   wherein the nanostructure comprises a nanotube.

2. Apparatus according to claim 1 wherein the nanostructure comprises a hollow nanotube containing a magnetic material.

3. Molecular delivery apparatus comprising:
   a molecular delivery vehicle comprising an elongated nanostructure having a longitudinal axis, and
   (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
   (ii) configured to receive at least one molecule of biological interest and hold the at least one molecule to the nanostructure;
   wherein the nanostructure comprises a nanotube; and
   wherein the nanostructure comprises a nanotube at least partially coated with a magnetic material.

4. Molecular delivery apparatus comprising:
   a molecular delivery vehicle comprising an elongated nanostructure having a longitudinal axis, and
   (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
   (ii) configured to receive at least one molecule of biological interest and hold the at least one molecule to the nanostructure;
   wherein the nanostructure comprises a nanotube; and
   wherein the nanostructure is at least partially coated with a mediating layer for immobilizing the molecules of biological interest.

5. Molecular delivery apparatus comprising:
   a molecular delivery vehicle comprising an elongated nanostructure having a longitudinal axis, and
   (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
   (ii) configured to receive at least one molecule of biological interest and hold the at least one molecule to the nanostructure;
   wherein the nanostructure comprises a nanotube; and
   wherein the at least one molecule of biological interest is a ligand in a biomembrane.

6. Apparatus according to claim 1 wherein at least one of the molecules of biological interest comprises a molecule that can cause a cellular response upon contact with cells.

7. Apparatus according to claim 1 wherein at least one of the molecules of biological interest comprises a molecule that can interact with intracellular molecules.

8. Molecular delivery apparatus comprising:
   a molecular delivery vehicle comprising an elongated nanostructure having a longitudinal axis, and
   (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
   (ii) configured to receive at least one molecule of biological interest and hold the at least one molecule to the nanostructure;
   wherein the nanostructure comprises a nanotube; and
   wherein the at least one molecule of biological interest comprises a molecule for imaging cellular structures or functions.

9. Molecular delivery apparatus comprising:
   a molecular delivery vehicle comprising an elongated nanostructure having a longitudinal axis, and
   (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
   (ii) configured to receive at least one molecule of biological interest and hold the at least one molecule to the nanostructure;
   wherein the nanostructure comprises a nanotube;
   wherein the at least one molecule of biological interest is immobilized on the nanostructure; and
   wherein the at least one molecule of biological interest is immobilized on the nanostructure by covalent linkage.

10. Molecular delivery apparatus comprising:
    a molecular delivery vehicle comprising an elongated nanostructure having a longitudinal axis, and
    (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
    (ii) configured to receive at least one molecule of biological interest and hold the at least one molecule to the nanostructure;
    wherein the nanostructure comprises a nanotube;
    wherein the at least one molecule of biological interest is immobilized on the nanostructure; and
    wherein the at least one molecule of biological interest is immobilized on the nanostructure by electrostatic forces.

11. Molecular delivery apparatus comprising:
    a molecular delivery vehicle comprising an elongated nanostructure having a longitudinal axis, and
    (i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
    (ii) configured to receive at least one molecule of biological interest and hold the at least one molecule to the nanostructure;

wherein the nanostructure comprises a nanotube;
wherein the at least one molecule of biological interest is immobilized on the nanostructure; and
wherein the at least one molecule of biological interest is immobilized on the nanostructure by hydrophobic attraction.

12. Apparatus according to claim 1 wherein the nanostructure is hollow, and further wherein at least one molecule of biological interest is contained within the hollow nanostructure.

13. Apparatus according to claim 3 further comprising a body of fluid, and further wherein the molecular delivery vehicle is suspended in the body of fluid.

14. Apparatus according to claim 3 further comprising at least one target cell, and further wherein the at least one target cell is immersed in the body of fluid.

15. Molecular delivery apparatus comprising:
a molecular delivery vehicle comprising an elongated nanostructure having a longitudinal axis, and
(i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
(ii) configured to receive at least one molecule of biological interest and hold the at least one molecule to the nanostructure; and
apparatus for establishing a magnetic field having a gradient;
wherein the nanostructure comprises a nanotube; and
wherein the magnetic field is changing.

16. Molecular delivery apparatus comprising:
a molecular delivery vehicle comprising an elongated nanostructure having a longitudinal axis, and
(i) configured so as to be oriented and driven by an appropriate magnetic field having a gradient, such that the elongated nanostructure can be oriented by the magnetic field so that its longitudinal axis extends in a desired direction, and such that the nanostructure can be moved in that desired direction by the magnetic field; and
(ii) configured to receive at least one molecule of biological interest and hold the at least one molecule to the nanostructure; and
apparatus for establishing a magnetic field having a gradient;
wherein the nanostructure comprises a nanotube; and
wherein the magnetic field is static.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: Rattus sp.

<400> SEQUENCE: 1
gagcaccagg ttgagcatga agaag                              25

<210> SEQ ID NO 2
<211> LENGTH: 25
<212> TYPE: DNA
<213> ORGANISM: Rattus sp.

<400> SEQUENCE: 2
cttcttcatg ctcaacctgg tgctc                              25

<210> SEQ ID NO 3
<211> LENGTH: 25
<212> TYPE: DNA
<213> ORGANISM: Rattus sp.

<400> SEQUENCE: 3
taccatggcc acacacaacg tgttc                              25